(12) United States Patent
Kainosho et al.

(10) Patent No.: US 7,608,248 B2
(45) Date of Patent: *Oct. 27, 2009

(54) STABLE ISOTOPE-LABELED AROMATIC AMINO ACIDS, METHOD FOR INCORPORATING THE SAME IN TARGET PROTEIN AND METHOD FOR NMR-STRUCTURAL ANALYSIS OF PROTEINS

(75) Inventors: Masatsune Kainosho, Tokyo (JP); Tsutomu Terauchi, Sagamihara (JP)

(73) Assignee: Japan Science and Technology Agency, Saitama (JP)

( * ) Notice: Subject to any disclaimer, the term of this patent is extended or adjusted under 35 U.S.C. 154(b) by 93 days.

This patent is subject to a terminal disclaimer.

(21) Appl. No.: 11/414,756

(22) Filed: Apr. 28, 2006

(65) Prior Publication Data

US 2006/0194328 A1  Aug. 31, 2006

Related U.S. Application Data

(63) Continuation of application No. PCT/JP2004/016215, filed on Nov. 1, 2004.

(30) Foreign Application Priority Data

Oct. 31, 2003  (JP) .............................. 2003-373304

(51) Int. Cl.
  *A61B 5/055* (2006.01)
  *C12P 13/04* (2006.01)
  *C12P 9/00* (2006.01)
  *C07K 1/00* (2006.01)
(52) U.S. Cl. ...................... 424/9.34; 435/106; 435/131; 530/350
(58) Field of Classification Search .................. 424/9.34
  See application file for complete search history.

(56) References Cited

U.S. PATENT DOCUMENTS 7,022,310 B2 * 4/2006 Kainosho et al. ........... 424/9.34

FOREIGN PATENT DOCUMENTS

WO  WO 94/18339  8/1994
WO  WO 99/11589  3/1999

OTHER PUBLICATIONS

Venters, et al. Journal of Biomolecular NMR, 5 (1995) pp. 339-344.*
Sattler, et al. Structure, 4 (1996) pp. 1245-1249.*

Takuya Torizawa et al.; NMR Assignment Methods for the Aromatic Ring Resonances of Phenylalanine and Tyrosine Residues in Proteins; J. Am. Chem. Soc.; 2005; vol. 127; No. 36; pp. 12620-12626.
Frank Lohr, et al.; Sequence-specific assignment of histidine and tryptophan ring $^1$H, $^{13}$C and $^{15}$N resonances in $^{13}$C/$^{15}$N- and $^2$H/$^{13}$C/$^{15}$N-labelled proteins; J. Biomol NMR 22; pp. 153-164; 2002.
Frank Lohr et al.; Novel Pulse Sequences for the Resonance Assignment of Aromatic Side Chains in $^{13}$C-Labeled Proteins; J. Mag. Res. Series B. 112, pp. 259-268; 1996.
Jeanine J. Prompers et al; Two-Dimensional NMR Experiments for the Assignment of Aromatic Side Chains in $^{13}$C-labeled Proteins; J. Mag. Res 130 ; pp. 68-75; 1998.
Toshihiko Yamazaki et al; Two Dimensional NMR Experiments for Correlating $^{13}$C β and $^1$Hδ/ε Chemical Shifts of Aromatic Residues in $^{13}$C-Labeled Proteins via Scalar Couplings; J. Am. Chem, Soc. 115; pp. 11054-11055; 1993.
Database Crossfire Beilstein, Beilstein Institute Zur Foerderung der Cheemischen Wissenschaften, Frankfurt AM Main, De; XP002442747; J. Magn. Res., vol. 163, No. 1, 2003, pp. 118-191.
Database Crossfire Beilstein, Beilstein Institut Zur Foerderung der Chemischen Wissenschaften, Frankfurt AM Main, DE; J. Am. Chem. Soc., vol. 123, No. 20, 2001, pp. 4803-4809.

* cited by examiner

*Primary Examiner*—Rebecca L Anderson
*Assistant Examiner*—Shawquia Young
(74) *Attorney, Agent, or Firm*—Hoffmann & Baron, LLP

(57) ABSTRACT

The present invention herein provides, for instance, a stable isotope-labeled phenylalanine wherein a carbon atom of the phenyl group linked to an amino acid residue is $^{13}$C, 2 to 4 carbon atoms of the remaining 5 carbon atoms constituting the phenyl group are $^{12}$C atoms to which deuterium atoms are bonded, and the remaining carbon atoms are $^{13}$C atoms to which hydrogen atoms are linked, and a stable isotope-labeled tyrosine wherein a carbon atom of the phenyl group linked to an amino acid residue is $^{13}$C, the carbon atom bonded to the hydroxyl group (OH group) of the phenyl group is $^{12}$C or $^{13}$C, 2 to 4 carbon atoms of the remaining 4 carbon atoms constituting the phenyl group are $^{12}$C atoms to which deuterium atoms are bonded, and the remaining carbon atoms are $^{13}$C atoms to which hydrogen atoms are linked. The stable isotope-labeled amino acid permits the elimination of such a conventional problem concerning the complexity of the NMR signals ascribed to aromatic rings, the complexity being a principal cause of making the NMR analysis difficult, encountered when using the conventional uniformly labeled amino acid residue. Moreover, the isotope-labeled amino acid likewise permits the substantial improvement of the sensitivity thereof to the NMR spectroscopic analysis.

2 Claims, 16 Drawing Sheets

STABLE ISOTOPE-LABELED AROMATIC AMINO ACIDS, METHOD FOR INCORPORATING THE SAME IN TARGET PROTEIN AND METHOD FOR NMR-STRUCTURAL ANALYSIS OF PROTEINS

CROSS-REFERENCE TO RELATED APPLICATIONS

This application is a continuation of International Application No. PCT/JP2004/016215, filed Nov. 1, 2004, which claims priority to Japanese Patent Application No. 2003-373304, filed Oct. 31, 2003, the contents of each of which are incorporated herein by reference.

TECHNICAL FIELD

The present invention relates to a stable isotope-labeled aromatic amino acid useful in the NMR spectroscopic structural analysis of proteins, a method for the incorporation of the amino acids into a target protein and a method for the structural analysis of a protein through the NMR spectrometric technique.

BACKGROUND ART

The structural analysis of a protein by the NMR spectrometry should always be carried out while taking into consideration such problems as any possible overlapping between NMR signals and the reduction of signal intensities due to the relaxation phenomenon. In this respect, it would be essential to the solution of this problem to develop an advanced NMR measurement and analysis technique. However, proteins each having a molecular weight on the order of about 20,000 can presently be analyzed without being accompanied by any significant error because of the application of the multinuclear and multi-dimensional NMR spectroscopic technique developed in the early 1990s to the protein and the development of a technique for the mass-production of stable isotope-labeled proteins, which has been advanced along with the progress of the NMR spectroscopic technique.

However, all of these methods are ones for obtaining information on the three-dimensional structure of a high molecular weight protein at the sacrifice of the precision of the determination of the higher-order structure thereof. Therefore, these techniques are limited in the subject to be analyzed and the effectiveness thereof In this respect, Patent Document 1 specified below discloses an invention which can solve these conventional problems, which permits the deuterium-exchange of a protein without adversely affecting the sensitivity of the remaining hydrogen nuclei to the NMR spectroscopic measurement and which simultaneously permits the rapid and highly reliable analysis of the NMR spectra observed for a protein having a molecular weight higher than the conventional limit and the determination of the higher-order structure thereof with a high accuracy. However, this invention never specifies the isotope-labeling pattern on the aromatic ring portion present in an aromatic amino acid.

On the other hand, aromatic amino acids such as Phe, Tyr and Trp play important roles along with the amino acids each carrying a long chain alkyl group such as Leu, Val and Ile in the formation of the three-dimensional structure of the hydrophobic core portion contained in a globular protein. In addition, these aromatic amino acids likewise play important roles in the manifestation of protein functions typical of the substrate-recognizing function, while making the most use of functional groups such as the hydroxyl group of Tyr and the nitrogen derived from the indole ring of lip, or the π-electrons common to the aromatic rings, in addition to the roles in the formation of the three-dimensional structure. In this respect, however, if using a sample uniformly labeled with stable isotope ($^{13}C$, $^{15}N$, $^{2}H$) disclosed in Patent Document 1 or a sample (non-labeled) having a natural abundance ratio of isotopes, the proton NMR signals, ascribed to the ring portions of the aromatic amino acids, in particular, Phe and Th), show chemical shifts quite close to one another and the chemical shifts of the carbon atoms ($^{13}C$) to which they are bonded likewise come close to one another. Accordingly, quite complicated signals are obtained for such a uniformly labeled derivative, this accordingly results in the deterioration of the sensitivity thereof to the NMR spectroscopic measurement and this makes, quite difficult, the individual observation of signals and the assignment thereof to each corresponding sequence.

Under such circumstances, there have been proposed a variety of methods for overcoming these difficulties, for collecting the information of nuclear Overhauser effects (NOE) concerning aromatic ring protons serving as the distance-limiting information quite important for the determination of the three-dimensional structure and for accurately measuring information on the local structure of aromatic rings. However, all of the conventional methods are ones developed while aiming at the sample uniformly labeled with stable isotope ($^{13}C$, $^{15}N$, $^{2}H$), whose preparation is quite easy and therefore, there has not yet been developed any method quite excellent from the viewpoint of the practicability.

Patent Document 1: International Publication WO 03/053910A1

DISCLOSURE OF THE INVENTION

It is an object of the present invention to provide a stable isotope-labeled aromatic amino acid. The labeled amino acid permits the elimination of such a conventional problem concerning the complexity of the NMR signals ascribed to aromatic rings, the complexity being a principal cause of making the NMR analysis difficult, encountered when using the conventionally developed uniformly isotope-labeled amino acid residues, and it likewise permits the substantial improvement of the sensitivity thereof to the NMR spectroscopic measurement.

It is another object of the present invention to provide an aromatic amino acid having a labeled pattern which allows the chain-assignment of the signals originated from the main chain to extend even to the assignment of the ring portions.

It is still another object of the present invention to provide a combination of stable isotope-labeled amino acids in which all of the amino acids constituting a target protein are completely replaced with stable isotope-labeled amino acids.

It is a further object of the present invention to provide a method for incorporating a stable isotope-labeled amino acid into a target protein.

It is a still further object of the present invention to provide a method for preparing a target protein constituted by stable isotope-labeled amino acids.

It is a still further object of the present invention to provide an NMR spectrometry method for determining protein structure, which can further be improved in the sensitivity.

The inventors of this invention have conducted various investigations, for the achievement of the foregoing objects, have found that the complexity observed not only in $^1H$-NMR spectra, but also in $^{13}C$-NMR spectra originated from the higher-order spin-spin coupling can be eliminated by sufficiently ensuring the magnetization-moving path originated from the remote $^{13}C$—$^{13}C$ and remote $^{13}C$—$^1H$ spin-spin coupling while taking into consideration the correlation of the sequential assignment of the NMR signals originated from the main chain through the C β carbon signal, and in other words, if the chemical shifts of directly linked carbon atoms may come close to one another at a high probability, the foregoing complexity can be eliminated by avoiding the labeling of these two carbon atoms with $^{13}C$ and simultaneously subjecting the hydrogen atoms on the non-labeled ($^{12}C$) carbon atoms to selective deuteration, and have thus completed the present invention.

According to the present invention, there is thus provided a stable isotope-labeled aromatic amino acid selected from those listed below:

A stable isotope-labeled phenylalanine wherein a carbon atom of the phenyl group linked to an amino acid residue represented by the following general formula A is $^{13}C$, 2 to 4 carbon atoms of the remaining 5 carbon atoms constituting the phenyl group are $^{12}C$ atoms to which deuterium atoms are bonded, and the remaining carbon atoms are $^{13}C$ atoms to which hydrogen atoms are linked;

A stable isotope-labeled tyrosine wherein a carbon atom of the phenyl group linked to an amino acid residue represented by the following general formula A is $^{13}C$, the carbon atom bonded to the hydroxyl group (OH group) of the phenyl group is $^{12}C$ or $^{13}C$, 2 to 4 carbon atoms of the remaining 4 carbon atoms constituting the phenyl group are $^{12}C$ atoms to which deuterium atoms are bonded, and the remaining carbon atoms are $^{13}C$ atoms to which hydrogen atoms are linked;

A stable isotope-labeled tryptophan wherein a carbon atom of the indolyl group linked to an amino acid residue represented by the following general formula A is $^{13}C$, 1 to 5 carbon atoms of the remaining 7 carbon atoms constituting the indolyl group are $^{12}C$ atoms to which deuterium atoms are bonded, the remaining carbon atoms are $^{13}C$ atoms to which hydrogen atoms are linked, and the nitrogen atom of the NH group constituting the indolyl group is $^{15}N$ or $^{14}N$; and A stable isotope-labeled histidine wherein a carbon atom of the imidazolyl group linked to an amino acid residue represented by the following general formula A is $^{13}C$, the both of the remaining two carbon atoms constituting the imidazolyl group are $^{13}C$ atoms to which hydrogen atoms are linked or one of these two carbon atoms is $^{12}C$ to which a deuterium atom is bonded, while the other carbon atom is $^{13}C$ to which a hydrogen atom is linked, one of the two nitrogen atoms constituting the imidazolyl group is $^{15}N$, while the other nitrogen atom is $^{14}N$, and the hydrogen atom constituting the NH group is not a deuterium atom:

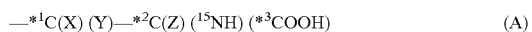

wherein each of *$^1$C, *$^2$C, and *$^3$C represents $^{12}C$ or $^{13}C$ atom, each of X, Y and Z represents a hydrogen or deuterium atom.

According to the present invention, there is also provided a combination of stable isotope-labeled amino acids constituting a target protein wherein the aromatic amino acids constituting the target protein are stable isotope-labeled aromatic amino acids specified above and the aliphatic amino acids constituting the target protein are stable isotope-labeled aliphatic amino acids which satisfy the following requirements of labeled patterns:

(a) In case where a methylene group carrying two hydrogen atoms is present, one of the methylene hydrogen atoms is deuterated;

(b) In case where a prochiral gem-methyl group is present, all of the hydrogen atoms on one of the methyl groups are completely deuterated, while the hydrogen atoms on the other methyl group are partially deuterated;

(d) In case where a methyl group other than the foregoing ones is present, all of the hydrogen atoms on the methyl group except for one hydrogen atom are deuterated or all of the hydrogen atoms on the methyl group are deuterated;

(e) After the deuteration in the foregoing items (a), (b) and (d), not less than 15 atom % of the carbon atoms of hydrogen atom-carrying methylene and/or methyl groups are replaced with $^{13}C$ atoms or all of the carbon atoms are $^{12}C$ atoms; and (f) All of the nitrogen atoms present are completely replaced with $^{15}N$ atoms.

The present invention also relates to a method for incorporating the foregoing stable isotope-labeled aromatic amino acids into a target protein, wherein the stable isotope-labeled aromatic amino acids are incorporated into the target protein through the cell-free protein synthesis.

The present invention likewise relates to a method for preparing a target protein constituted by stable isotope-labeled amino acids, wherein the method comprises the step of carrying out cell-free protein synthesis, using a combination of the foregoing stable isotope-labeled amino acids as the whole amino acids constituting the target protein.

The present invention also provides a method for the NMR spectrometric structural analysis of a protein, wherein the method comprises the steps of incorporating the stable isotope-labeled aromatic amino acids into the target protein and measuring NMR spectra on the target protein to thus carry out the structural analysis thereof.

The present invention likewise provides a method for analyzing the structure of a target protein using the NMR technique, wherein the method comprises the steps of analyzing the structure of the target protein in which all of the amino acids constituting the same are replaced with the foregoing stable isotope-labeled amino acids according to the NMR spectrometry.

BEST MODE FOR CARRYING OUT THE INVENTION

Figure 1:
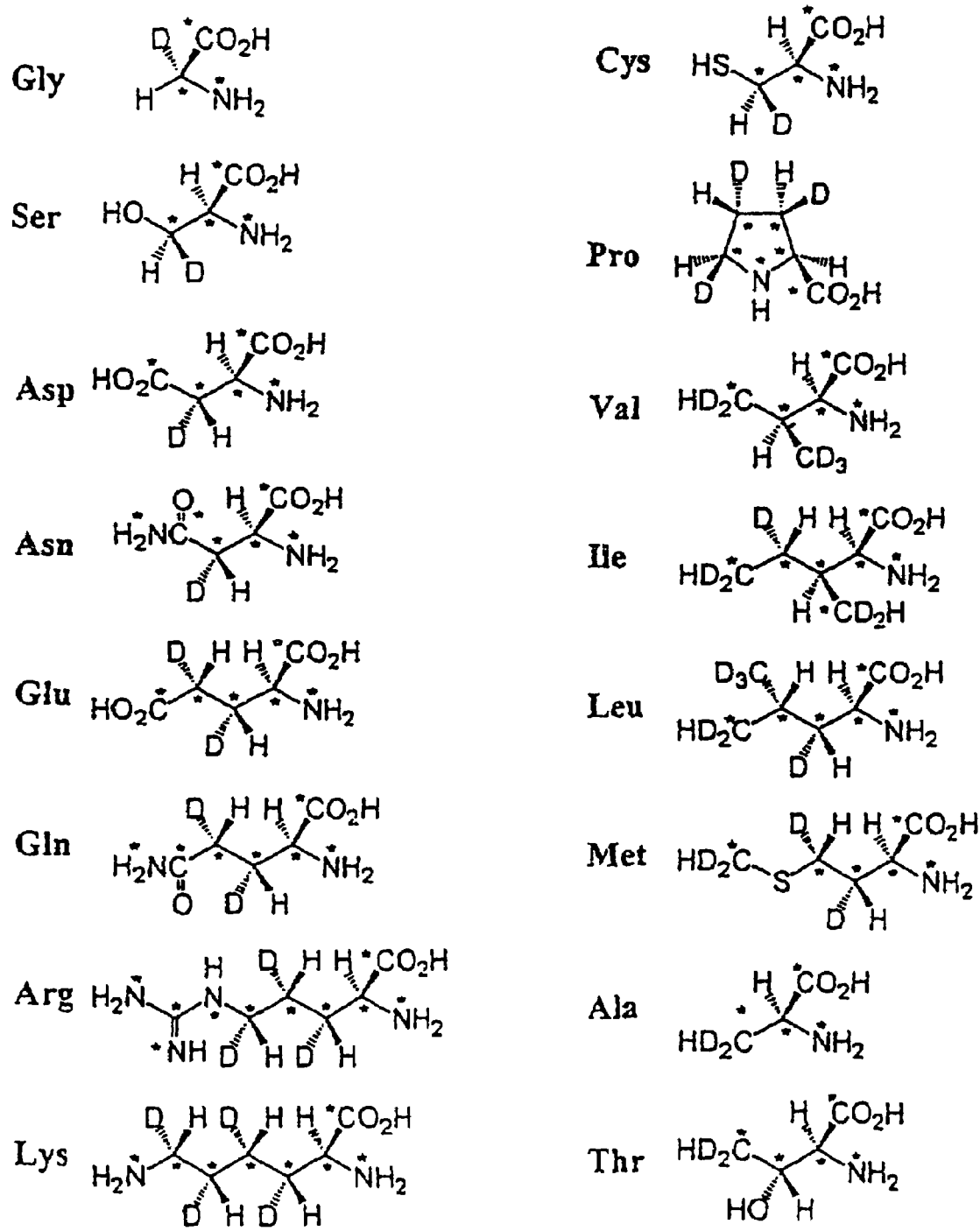
FIG. 1 shows stable isotope-labeled aliphatic amino acids preferably used in the present invention.

In the present invention, the complexity observed not only in the $^1$H-NMR spectrometry, but also in the $^{13}$C-NMR spectrometry because of the higher-order spin-spin coupling can fundamentally be eliminated, by avoiding the labeling, with $^{13}$C, of two carbon atoms directly linked together, whose chemical shifts come close to one another at a high probability, and by simultaneously selectively deuterating the hydrogen atoms on the non-labeled ($^{12}$C) carbon atoms, and furthermore the amino acid should be designed so as to sufficiently ensure the magnetization-moving path originated from the remote $^{13}$C—$^{13}$C and remote $^{13}$C—$^1$H spin-spin coupling while taking into consideration the correlation of the sequential assignment of the NMR signals originated from the main chain through the C β carbon signal. Accordingly, the following three kinds of isotope-labeled amino acids are designed for phenylalanine (Phe) and synthesized:

(1) [γ, ε 1, ε 2-$^{13}$C$_3$; δ 1, δ 2, ζ-$^2$H$_3$]-Phe: This is so designed as to aim at the establishment of the correlation of the chemical shifts of ring protons with C β or the NMR signals of the main chain while making use of the fact that the spin-spin coupling constant between $^1$H ε-$^{13}$C γ is relatively high on the order of about 7 Hz.

(2) [γ, ζ-$^{13}$C$_2$; δ 1, δ 2, ε 1, ε 2-$^2$H$_4$]-Phe: This is so designed as to aim at the establishment of the correlation of the chemical shifts of ring protons with C β or the NMR signals of the main chain while making use of the fact that the spin-spin coupling constant between $^{13}$C ζ-$^{13}$C β is relatively high on the order of about 9 Hz.

(3) [γ, δ 1, δ 2-$^{13}$C$_3$; ε 1, ε 2, ζ-$^2$H$_3$]-Phe: This is so designed as to aim at the establishment of the correlation of the chemical shifts of ring protons with C β or the NMR signals of the main chain while making use of a large spin-spin coupling between $^{13}$C δ-$^{13}$C γ (about 60 Hz).

In any case, the spin-spin coupling between protons is not observed at all and therefore, various advantages can be expected, in the NMR spectrometric analysis. For instance, the resulting NMR spectra are accordingly considerably simplified and the sensitivity of the NMR spectrometric analysis is likewise considerably improved.

As to tyrosine (Tyr), a hydroxyl group is linked to the carbon atom present at z-position and accordingly, the $^1$H-NMR signals are, by nature, relatively simple, but the following two kinds of isotope-labeled amino acids are designed and synthesized, like the foregoing phenylalanine (Phe). The following amino acids (3), (4) show completely the same efficacy:

(3) [γ, ε 1, ε 2-$^{13}$C$_3$; δ 1, δ 2-$^2$H$_2$]-Tyr;
(4) [γ, δ 1, δ 2-$^{13}$C$_3$; ε 1, ε 2-$^2$H$_2$]-Tyr

Tryptophan (Trp) has a ring moiety which is unsymmetrical bicyclic structure and accordingly, a large number of factors should be taken into consideration, but the following amino acid is designed and synthesized:

(5) [ζ 2, ζ 3; γ, δ, ε 1, ε 2, η2]-Tyr

The present invention is completely different, in conception, from the labeled pattern of the isotope-labeled aromatic amino acid disclosed in Patent Document 1 in that the amino acid should be designed so as to sufficiently ensure the magnetization-moving path originated from the remote $^{13}$C—$^{13}$C and remote $^{13}$C—$^1$H spin-spin coupling while taking into consideration the correlation of the sequential assignment of the NMR signals originated from the main chain through the C β carbon signal.

In Patent Document 1, when at least two magnetically equivalent $^1$H nuclei such as methyl groups are present, the hydrogen atoms except for one are deuterated. Similarly, the nuclei of hydrogen atoms at δ 1, δ 2-positions and ε 1, ε 2-positions are magnetically equivalent in Phe and Tyr, respectively and therefore, each of these amino acids has such a labeling pattern that only one of the hydrogen nuclei arranged at δ-positions or ε-positions is deuterated. However, it would in general be quite difficult for each three-dimensional structure of the aromatic ring portion on an amino acid side chain present in a protein to rotate about β-γ axis (around two axes) unlike the methyl group and accordingly, the protons on an aromatic ring are recognized not to be magnetically equivalent. For this reason, if a protein is structurally analyzed using Phe and Tyr disclosed in Patent Document 1, the sensitivity of the protons on the aromatic ring portion to the NMR spectrometry may be reduced even when comparing the same with that observed for the conventional technique. The labeling pattern up to the β-position may be the same as that disclosed in Patent Document 1.

The stable isotope-labeled aromatic amino acids preferably used in the present invention are as follows:

A stable isotope-labeled phenylalanine wherein a carbon atom of the phenyl group linked to an amino acid residue represented by the foregoing general formula A is $^{13}$C, 3 or 4 carbon atoms of the remaining 5 carbon atoms constituting the phenyl group are $^{12}$C atoms to which deuterium atoms are bonded, and the remaining carbon atoms are $^{13}$C atoms to which hydrogen atoms are linked;

A stable isotope-labeled tyrosine wherein a carbon atom of the phenyl group linked to an amino acid residue represented by the foregoing general formula A is $^{13}$C, the carbon atom bonded to the hydroxyl group (OH group) of the phenyl group is $^{12}$C or $^{13}$C, 3 or 4 carbon atoms of the remaining 4 carbon atoms constituting the phenyl group are $^{12}$C atoms to which deuterium atoms are bonded, and the remaining carbon atoms are $^{13}$C atoms to which hydrogen atoms are linked;

A stable isotope-labeled tryptophan wherein a carbon atom of the indolyl group linked to an amino acid residue represented by the foregoing general formula A is $^{13}$C, 3 to 5 carbon atoms of the remaining 7 carbon atoms constituting the indolyl group are $^{12}$C atoms to which deuterium atoms are bonded, the remaining carbon atoms are $^{13}$C atoms to which hydrogen atoms are linked, and the nitrogen atom of the NH group constituting the indolyl group is $^{15}$N or $^{14}$N; and A stable isotope-labeled histidine wherein a carbon atom of the imidazolyl group linked to an amino acid residue represented by the foregoing general formula A is $^{13}$C, one of the remaining two carbon atoms constituting the imidazolyl group is $^{12}$C to which a deuterium atom is bonded, while the other carbon atom is $^{13}$C to which a hydrogen atom is linked, one of the two nitrogen atoms constituting the imidazolyl group is $^{15}$N, while the other nitrogen atom is $^{14}$N, and the hydrogen atom constituting the NH group is not a deuterium atom.

In the stable isotope-labeled aromatic amino acids used in the present invention, it is preferred that each of *$^1$C, *$^2$C, and *$^3$C appearing in the amino acids represented by the general formula A is $^{13}$C atom. More preferably used herein are stable isotope-labeled aromatic amino acids represented by the following general formulas (1) to (15):

Phenylalanine
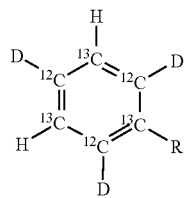
(1)
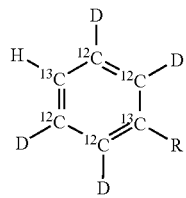
(2)
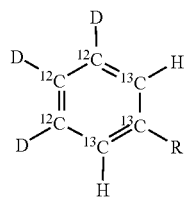
(3)
Tyrosine
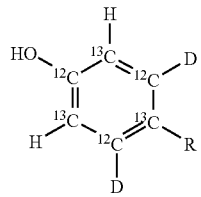
(4)
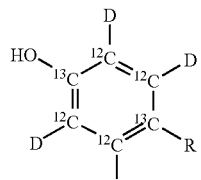
(5)
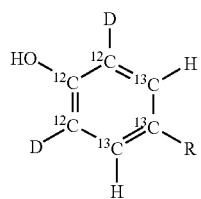
(7)
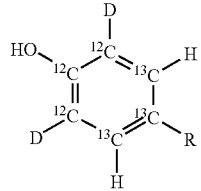
(8)
Tryptophan
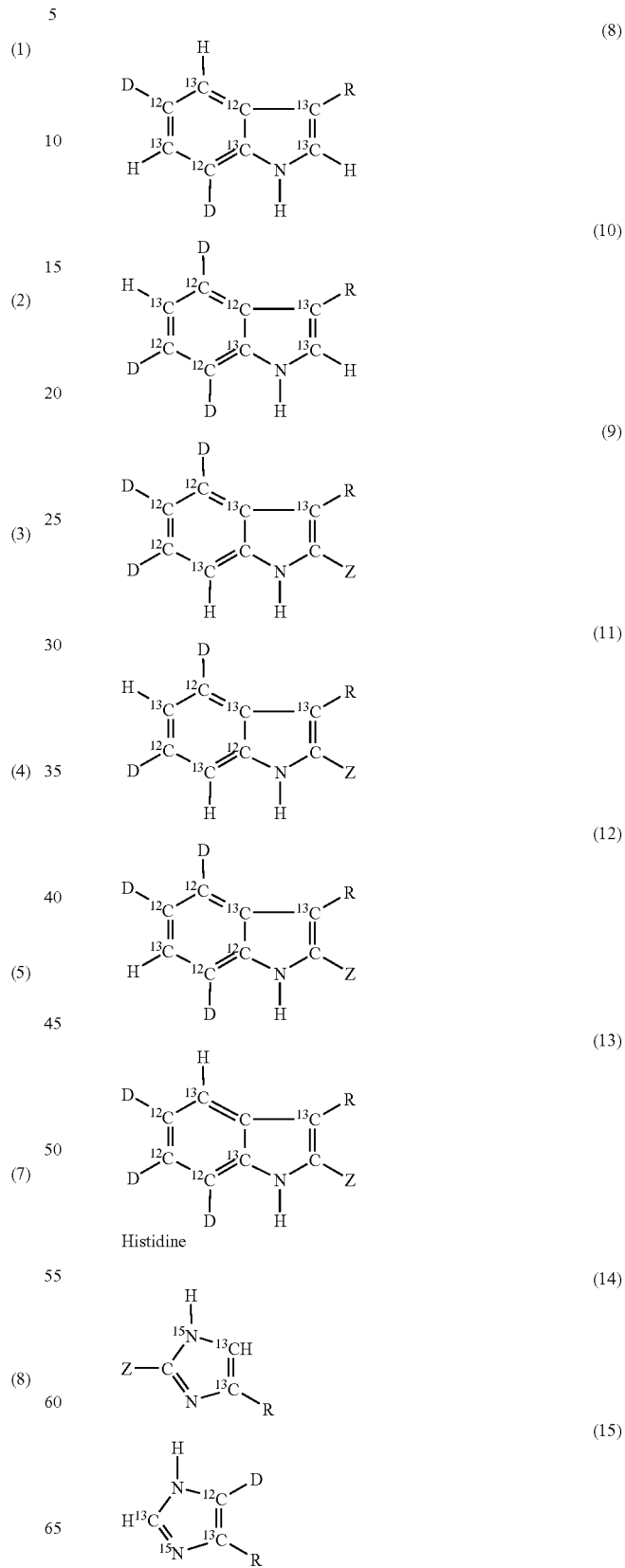

wherein, in these formulas, C represents $^{12}$C or $^{13}$C, N represents $^{14}$N or $^{15}$N, Z represents a hydrogen atom or a deuterium atom and R represents a group represented by the following formula:

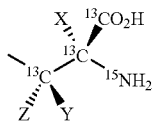

wherein, in the formula, each of X, Y and Z represents a hydrogen atom or a deuterium atom.

Among these compounds, particularly preferred are the stable isotope-labeled aromatic amino acids represented by the foregoing general formulas (1), (2), (3), (4), (7) or (8).

The stable isotope-labeled aromatic amino acids used in the present invention can be prepared by using any combination of a variety of conventionally known chemical synthesis methods or by the use of such a method modified. For instance, they can be chemically synthesized according to a reaction scheme as will be illustrated later in the following Example.

In the present invention, the foregoing stable isotope-labeled aromatic amino acids are used as the amino acid components constituting a target protein, the target protein is synthesized according to the cell-free protein synthesis method to thus give the intended target protein constituted by the stable isotope-labeled aromatic amino acids and the resulting target protein is analyzed by the NMR spectroscopy to thus structurally analyze the protein. In this respect, however, it is preferred to use the stable isotope-labeled aliphatic amino acids, which can satisfy the foregoing requirements of labeling pattern (a) to (f) as the aliphatic amino acid components constituting the target amino acids, in combination with the foregoing stable isotope-labeled aromatic amino acids.

In this connection, as the stable isotope-labeled aliphatic amino acids, which can satisfy the requirements of the labeling pattern (a) to (f), preferably used herein are those in which after the deuteration in the foregoing items (a), (b) and (d), all of the carbon atoms of hydrogen atom-carrying methylene and methyl groups are replaced with $^{13}$C atoms. In addition, the carbon atoms constituting the carbonyl and guanidyl groups of stable isotope-labeled aliphatic amino acids are replaced with $^{13}$C. Further, preferably used herein also include, for instance, those in which after the deuteration in the foregoing items (a), (b) and (d), the ratio $^{13}$C/$^{12}$C with respect to the carbon atoms of hydrogen atom-carrying methylene and methyl groups is 15/8 (as expressed in terms of the atomic ratio) or all of the carbon atoms are $^{12}$C atoms.

Incidentally, particularly preferred as the stable isotope-labeled aliphatic amino acids which can satisfy the requirement of the labeling pattern (a) to (f) are those represented by the structural formulae depicted in FIG. 1 of Patent Document 1 and these stable isotope-labeled aliphatic amino acids can easily be prepared according to the methods detailed in Patent Document 1. In this respect, the content of Patent Document 1 is assumed to be fully described in this specification. In FIG. 1, the stable isotope-labeled aliphatic amino acids include neutral amino acids and basic amino acids. For reference, the stable isotope-labeled aliphatic amino acids as depicted in FIG. 1 of Patent Document 1 are herein illustrated in the attached FIG. 1.

Stable isotope-labeled amino acids are incorporated into a target protein in order to conduct the structural analysis of the protein according to the NMR spectroscopy. At this stage, a member or a plurality of members arbitrarily selected from the group consisting of the aromatic amino acids constituting the target protein or all of the aromatic amino acids can be replaced with the stable isotope-labeled aromatic amino acids of the present invention each having an isotope-labeling pattern, which would permit the acquisition of information concerning the three-dimensional structures of the target protein as shown in this specification and which would make the NMR spectroscopic analysis thereof most efficient. However, it is herein preferred that all of the aromatic amino acids constituting the target protein are completely replaced with the stable isotope-labeled aromatic amino acids according to the present invention, while all of the remaining amino acids constituting the target protein or all of the aliphatic amino acids are likewise completely replaced with the foregoing isotope-labeled amino acids. The amino acids constituting the target protein can be replaced with the corresponding stable isotope-labeled amino acids according to any conventionally known method such as the usual high-expressive protein synthesis system (cell lines) which makes use of cultivated biological cells; an organic chemical-enzyme chemical peptide/protein synthesis method; or a protein-preparation method using a cell-free extract. Among these methods, preferably used herein is the protein-preparation method using a cell-free extract. This is because, the protein-preparation method never suffers from a problem such as the isotope-dilution due to amino acid metabolism possibly encountered when using the method which makes use of cultivated biological cells; permits easy control of the diffusion of isotopes; and likewise permits the highly efficient incorporation, into a target protein, of isotope-labeled amino acids whose mass-production is quite difficult.

A variety of methods can likewise be used for the spectroscopic measurement using the NMR technique and for the structural analysis of proteins. Further, it is also possible to, for instance, identify or specify the site suffering from any structural change or modification through the linkage with ligands.

In any case, the amino acids used in the present invention are principally characterized by the fact that each of them has a variety of isotope-labeled patterns and the incorporation thereof into a protein would permit the practice of the three-dimensional structural analysis of the protein. The conventional method may permit such structural analysis only with considerable difficulties.

The present invention permits the design of amino acids most suitably used for the acquisition of information concerning the three-dimensional structures of proteins by variously combining the stereo-selective deuteration (SSD), the regio-selective deuteration (RSD), the stereo-array deuteration (SAD), the proton-density minimization (PDM) and the tailored ring-labeling (TRL) disclosed in Patent Document 1.

The method for the structural analysis using the NMR technique according to the present invention is preferably a method for the NMR spectrometric structural analysis of a target protein comprising the step of analyzing, according to the NMR spectrometric measurement, the structure of a target protein in which all of the amino acids constituting the target protein are replaced with the foregoing stable isotope-labeled amino acids, or the aromatic amino acids are replaced with the foregoing stable isotope-labeled aromatic amino acids, while the amino acids other than the aromatic ones or the aliphatic amino acids are replaced with the foregoing stable isotope-labeled aliphatic amino acids.

The present invention permits the achievement of the effects given below. The dipole-dipole interaction can be reduced by labeling the amino acid residues present in a protein with deuterium atoms and this accordingly results in the improvement of the sensitivity of the protons on an aromatic ring and those present in the vicinity thereof to the NMR signal-measurement.

(i) The dipole-dipole interaction can be reduced by labeling the amino acid residues present in a protein with deuterium atoms and this accordingly results in the improvement of the sensitivity of the protons on an aromatic ring and those present in the vicinity thereof to the NMR signal-measurement.

(ii) The present invention allows the chain-assignment of the signals originated from the main chain to extend even to the assignment of the signals to ring portions and accordingly, this in turn permits the sequence-specific assignment of the signals originated from the aromatic ring.

(iii) The present invention permits the improvement of the precision of the NMR spectroscopic analysis.

(iv) The present invention permits the shortening of the time required for the NMR spectroscopic analysis.

(v) The present invention permits the collection of the information concerning NOE in which the aromatic ring-protons are involved and this in turn permits the more accurate determination of the three-dimensional structure of the core portions of proteins.

(vi) The present invention permits the determination of protein structures and the acquisition of information concerning the structures of proteins while making use of the signals originated from the side chains of aromatic amino acid residues and thus permits the acquisition of information of detailed structures in the proximity to the labeled amino acid residues of a specific protein.

(vii) Moreover, when the labeled aromatic amino acids according to the present invention are amino acid residue-selectively incorporated into a specific protein, it would be expected that the foregoing effects (i) to (vi) can be achieved.

The following Examples will illustrate the preparation of a protein labeled using amino acid having a variety of labeling patters and will likewise demonstrate various excellent characteristic properties provided by the NMR spectral data when obtaining the information concerning the three-dimensional structure of a specific protein.

Of course, the following Examples are given for understanding the present invention more specifically or in detail and the present invention is not restricted to these specific Examples at all.

EXAMPLE 1

Figure 2:
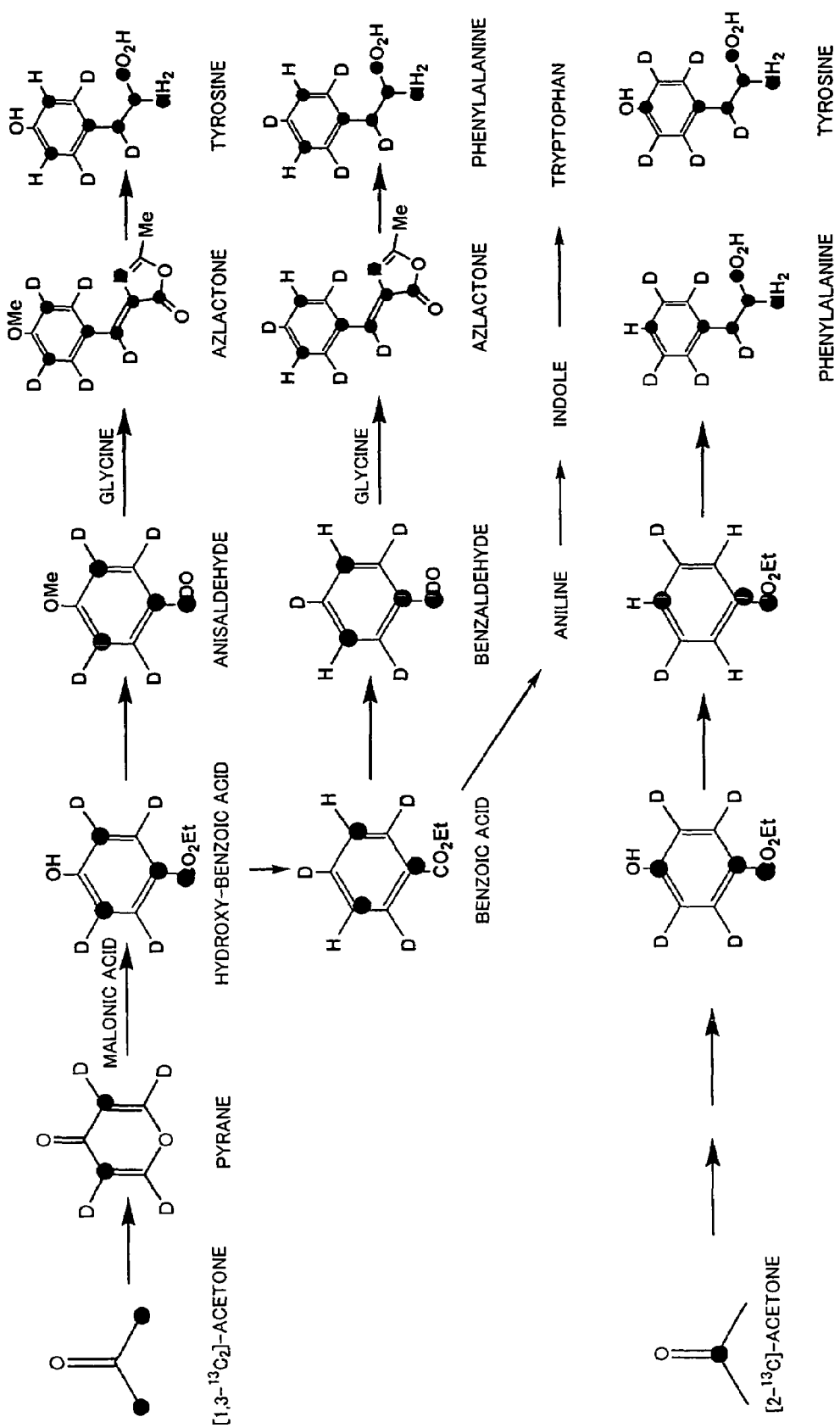
FIG. 2 is a schematic diagram showing the route for synthesizing stable isotope-labeled derivatives of phenylalanine, tyrosine and tryptophan starting from acetone.

Synthesis of Stable Isotope-Labeled Derivative of Phenylalanine, Tyrosine and Tryptophan FIG. 2 shows a flow chart illustrating the synthesis of stable isotope-labeled derivatives of phenylalanine, tyrosine and tryptophan starting from acetone.

Figure 3:
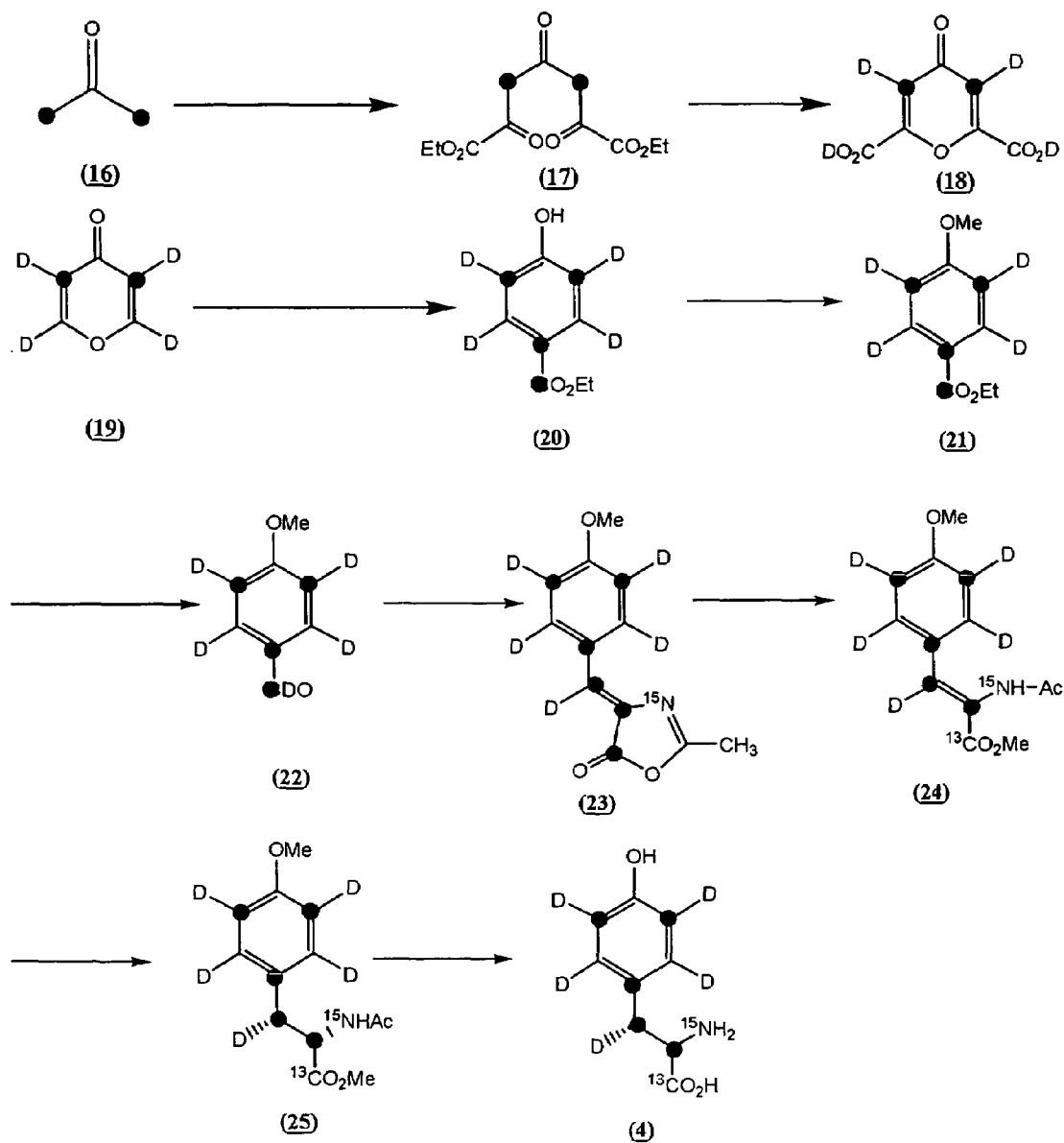
FIG. 3 is a diagram showing the route for synthesizing a stable isotope-labeled tyrosine (4) starting from acetone (16).

Synthesis of Stable Isotope-Labeled Tyrosine (4) from Acetone (16) (FIG. 3)

(i) [3,5-$^{13}C_2$]-Diethyl 2,4,6-Trioxoheptanoate (17)

The synthesis was carried out with reference to the disclosure of Reference Article (1). To a mixture of 10 g (167 mmol) of [1,3-$^{13}C_2$]-acetone (16) and 25 ml (184 mmol) of diethyl oxalate, there was dropwise added 65 ml (174 mmol) of a 21% solution of EtONa in ethanol over 2 hours in a water bath. After stirring at room temperature for one hour, 25 ml (184 mmol) of diethyl oxalate was added to the mixture and 65 ml (174 mmol) of a 21% EtONa solution in ethanol was dropwise added thereto in a water bath. Then the solvent was distilled off at 105° C. for 2 hours with stirring. To the resulting residue, there were added 40 ml of hydrochloric acid at 0° C. and then 140 ml of ice water, followed by the filtration thereof and the subsequent drying of the residue to thus give 27.8 g (107 mmol, 64%) of [3,5-$^{13}C_2$]-diethyl ester of 2,4,6-trioxo-heptanoic acid (17).

(ii) [3,5-$^{13}C_2$;1,3,5,7-$^2H_4$]-4-Oxo-4H-Pyrane-2,6-Dicarboxylic Acid (18)

The synthesis was carried out with reference to the disclosure of Reference Article (2). To 30 ml of conc. DCl, there was suspended 27.8 g (107 mmol) of the heptanoic acid ester, followed by stirring the suspension at 102° C. for 24 hours, cooling the same, filtration thereof, washing of the resulting residue with cold $D_2O$ (5 ml×2), introduction thereof into an autoclave, dissolution thereof in 200 ml of $D_2O$ and the subsequent stirring thereof at 120° C. for 12 hours. The resulting solution was cooled and then allowed to stand at room temperature over 12 hours to thus precipitate crystals. The crystals were filtered off, followed by the introduction of the residue into a beaker and the subsequent drying thereof at 110° C. for 2 hours and 160° C. for 2 hours in an oil bath to thus give 19.1 g (101 mmol, 94%) of the title compound: 4-oxo-4H-pyrane-2,6-dicarboxylic acid (18).

(iii) [3,5-$^{13}C_2$;2,3,5,6-$^2H_4$]-4H-Pyrane-4-One (19)

The synthesis was carried out with reference to the disclosure of Reference Article (2). Cu Powder (19.0 g) was treated with 10 ml of 2N DCl solution for one minute while applying ultrasonic waves, followed by decantation of the mixture, addition of 10 ml of $D_2O$ and then drying the mixture with heating at 160° C. for one hour. The resulting product was combined with 19.1 g (101 mmol) of the dicarboxylic acid (18), mixed together in a mortar, followed by addition of 15 ml of $D_2O$, heating thereof at 160° C. for one hour and then distillation thereof at ordinary pressure (while stepwise heating at 240° C. for one hour, 250° C. for one hour and 260° C. for 3 hours) to thus give 7.39 g (72.6 mmol, 72%) of the title compound: 4-oxo-4H-pyrane (19).

(iv) [1,3',5'-$^{13}C_3$; 2',3',5',6'-$^2H_4$]-Ethyl 4'-Hydroxybenzoate (20)

The synthesis was carried out with reference to the disclosure of Reference Article (3). There were dissolved, in 50 ml of t-BuOD, 7.39 g (72.6 mmol) of the pyrane (19) and 13.0 ml (79.8 mmol) of [1,2,3-13C3]-malonic acid ethyl ester, a solution of t-BuOK (2.9 g, 17.8 mmol) in t-BuOD (80 ml) was dropwise added to the solution at 105° C. over one hour. After stirring the mixture at 105° C. for 18 hours, the temperature thereof was brought back to room temperature, followed by addition of 150 ml of $D_2O$ and then 50 ml of a 2N DCl solution, concentration thereof under reduced pressure, addition of 500 ml of ethyl acetate and 100 ml of distilled water to thus make the mixture separate into two liquid phases, and the subsequent washing of the resulting organic phase with 100 ml of a saturated common salt solution. The organic phase was concentrated under reduced pressure and then purified by the silica gel chromatography (ethyl acetate: hexane=1:1) to thus give 10.7 g (61.4 mmol, 37%) of title compound: hydroxy-benzoate (20).

(v) [1,3',5'-$^{13}C_3$; 2',3',5',6'-$^2H_4$]-Ethyl 4'-Methoxy-benzoate (21)

The synthesis was carried out with reference to the disclosure of Reference Article (4). There was dissolved 3.39 g (19.4 mmol) of the hydroxy-benzoate (20) in 100 ml of dehydrated acetone, followed by addition of 1.56 ml (25.1 mmol) of methyl iodide and 12.1 g (87.6 mmol) of potassium carbonate to the resulting solution and then stirring at 75° C. for 16 hours in a nitrogen gas atmosphere. Distilled water (30 ml) was added to the solution, the resulting mixture was concentrated under reduced pressure to a volume of about 30 ml, the concentrate was then extracted with diethyl ether (50 ml×3), the extract was concentrated under reduced pressure and then the concentrate was purified by the silica gel chromatography (ethyl acetate: hexane=1:1) to thus give 3.40 g (18.1 mmol, 93%) of title compound: methoxy-benzoate (21).

(vi) [1,3',5'-$^{13}C_3$; 1,2',3',5',6'-$^2H_5$]-4'-Methoxy-benzaldehyde (22)

The synthesis was carried out with reference to the disclosure of Reference Article (4). There was dissolved 3.40 g (18.1 mmol) of the methoxy-benzoate (21) in 20 ml of dehydrated THF, and then 19 ml (19.0 mmol) of a 1M LiAlD$_4$ solution in THF was added to the solution at 0° C. After continuing the reaction of these components at room temperature for 30 minutes, 80 ml of a 1N HCl was added to the reaction system, the mixture was concentrated under reduced pressure to a volume of about 80 ml, the resulting concentrate was extracted with ethyl acetate (60 ml×3) and the extract was concentrated under reduced pressure to thus give methoxy-benzyl alcohol. The alcohol was dissolved in 200 ml of methylene chloride, 10 g of Molecular Sieves 4A and 3.89 g (36.2 mmol) of PCC were added to the resulting solution at 0° C., the mixture was stirred at 0° C. for 3 hours, packed in a 30 φ chromatography tube, 12 cm of Celite was added, followed by elution with 1000 ml of diethyl ether and concentration under reduced pressure to thus form 1.81 g (11.6 ml) of the title compound: methoxy-benzaldehyde (22).

(vii) [1,2,3,3',5'-$^{13}C_5$; 3,2',3',5',6'-$^2H_5$; 2-$^{15}N_1$]-4-Methoxy-benzylidene-azlactone (23)

The synthesis was carried out with reference to the disclosure of Reference Article (5). To 1.81 g (15.1 mmol) of [1,2-$^{13}C_2$; 2-$^{15}N_1$]-N-acetyl glycine, there were added 1.81 g (11.6 ml) of the methoxy-benzaldehyde (2), 900 mg (11.0 mmol) of sodium acetate and 3 ml of acetic acid anhydride, and then the resulting mixture was stirred at 105° C. for 14 hours in a nitrogen gas atmosphere. The resulting mixture was concentrated, the resulting crystals were filtered off in an ice bath, washed with cold water, dried under reduced pressure to thus give 1.23 g (5.3 mmol, 46%) of the title compound: 4'-methoxybenzylidene-azlactone (23).

(viii) [1,2,3,3',5'-$^{13}C_5$; 3,2',3',5',6'-$^2H_5$; 2-$^{15}N_1$]-dehydro-N-acetyl-4'-methoxyphenyl-alanine methyl ester (24)

The synthesis was carried out with reference to the disclosure of Reference Article (6). There was dissolved 1.23 g (5.3 mmol) of the azlactone (23) in 50 ml of dehydrated MeOH, 0.5 ml of triethylamine was added to the solution at room temperature, and then the resulting mixture was stirred at room temperature for one hour. After the solvent was distilled off under reduced pressure, the residue was loaded on a silica gel column (20×70 mm), followed by elution with 200 ml of ethyl acetate.

The solvent was distilled off from the resulting extract to thus give 1.03 g (3.9 mmol, 74%) of the intended dehydro-compound (24).

(ix) (2S,3R)-[1,2,3,3',5'-$^{13}C_5$; 3,2',3',5',6'-$^2H_5$; 2-$^{15}N_1$]-N-acetyl-4'-methoxyphenyl-alanine methyl ester (25)

The synthesis was carried out with reference to the disclosure of Reference Article (7). There was dissolved 1.03 g (3.9 mmol) of the dehydro-compound (24) in 15 ml of dehydrated methanol, 55 mg of (S,S)-Et-DuPhos-Rh catalyst was introduced into the solution and the resulting mixture was stirred at room temperature for 12 hours using a medium pressure reducing device at a hydrogen gas pressure of 2 atm. The resulting product was loaded on a silica gel column (15×40 mm), followed by elution with 200 ml of ethyl acetate to thus give 1.02 g (3.8, mmol 98%) of the intended compound: methoxyphenyl-alanine methyl ester (25).

(x) (2S,3R)-[1,2,3,3',5'-$^{13}C_5$; 3,2',3',5',6'-$^2H_5$; 2-$^{15}N_1$]-Tyrosine (26)

The synthesis was carried out with reference to the disclosure of Reference Article (8). There was dissolved 1.02 g (3.8 mmol) of the tyrosine methyl ester (2) in 50 ml of a 1N HCl solution, and then the resulting solution was stirred at 105° C. for 12 hours. After cooling, the resulting mixture was concentrated and then ion-exchanged using Dowex-50w-X8 to thus give 775 mg (3.77 mmol) of methoxyphenyl alanine. This alanine and 623 mg (4.15 mmol) of sodium iodide were dissolved in 45 ml of a 48% hydrobromic acid solution, the container was closed with a septum and firmly tightened with a wire and the content thereof was stirred at 92° C. for 4 hours. After cooling down to room temperature, the resulting mixture was concentrated and then ion-exchanged using Dowex-50w-X8 to thus give the title compound: tyrosine (4).

Figure 4:
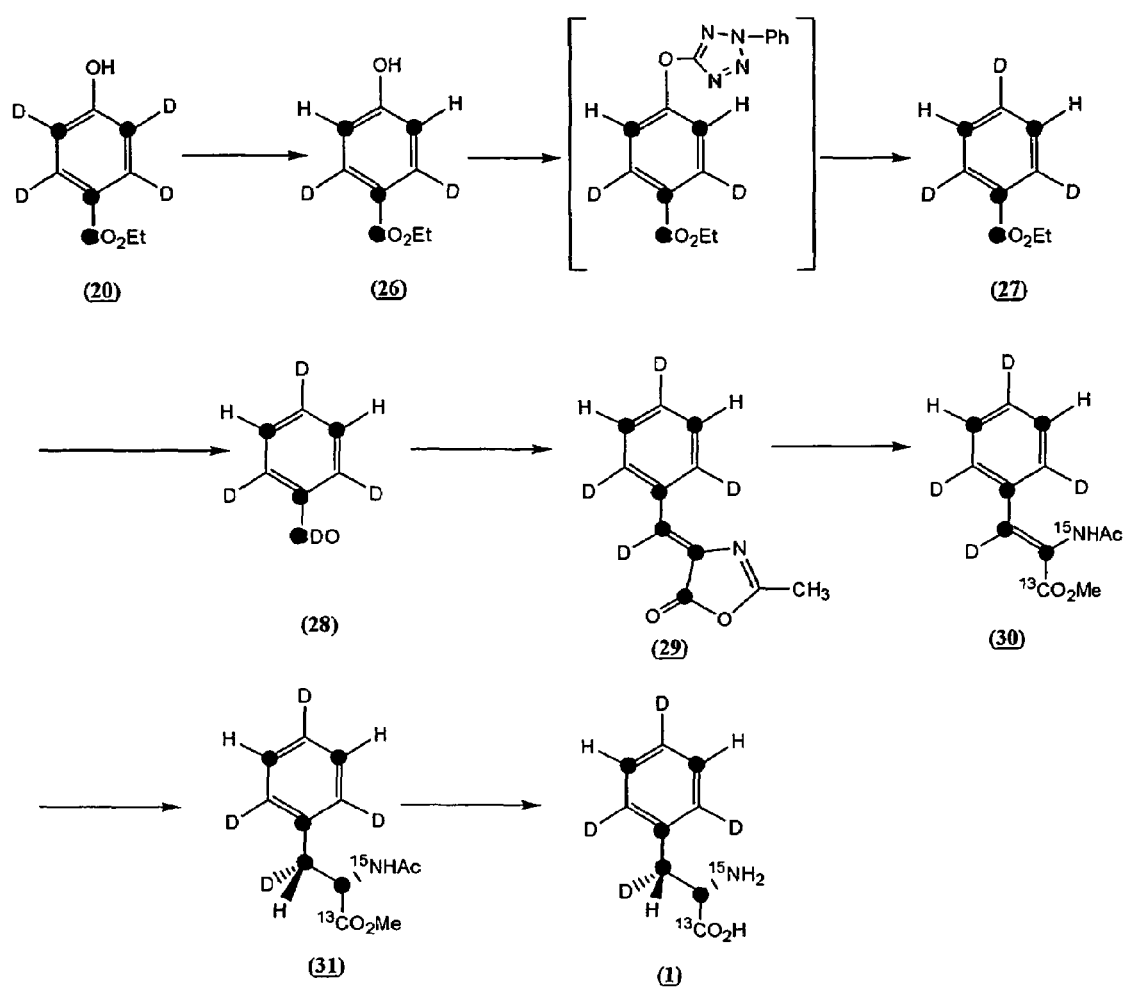
FIG. 4 is a diagram showing the route for synthesizing a stable isotope-labeled phenylalanine (1).

Synthesis of Stable Isotope-Labeled Phenylalanine
(FIG. 4)

(i) [1,3',5'-$^{13}C_3$; 2',6'-$^2H_2$]-Ethyl 4'-Hydroxybenzoate (26)

The synthesis was carried out with reference to the disclosure of Reference Article (9). There was suspended 3.8 g (21.9 mmol) of hydroxy-benzoic acid (20) in 80 ml of a 6N HCl, and then the resulting solution was stirred at 102° C. for 12 hours. After cooling, the solvent was distilled off from the solution, 660 μl of thionyl chloride and 10 ml of dehydrated ethanol were added to the resulting residue and this mixture was stirred at 90° C. for 4 hours. After the distillation off of the solvent, the resulting residue was purified by silica gel chromatography (ethyl acetate:hexane=1:1) to thus give 3.0 g (17.4 mmol, 80%) of hydroxy-benzoate (26).

(ii) [1,3',5'-$^{13}C_3$; 2',4',6'-$^2H_3$]-Ethyl Benzoate (27)

The synthesis was carried out with reference to the disclosure of Reference Article (10). There was dissolved 4.5 g (26.2 mmol) of the hydroxy-benzoate (26) in 120 ml of dehydrated acetone, 5.0 g (27.7 mmol) of 1-phenyl-5-chlorotetrazole and 22 g (159 mmol) of potassium carbonate were added to the resulting solution at room temperature and then the mixture was stirred at 75° C. for 15 hours. After the filtration of the mixture, the resulting filtrate was concentrated, the residue thus obtained was dissolved in 80 ml of EtOD, 3.5 g of a Pd—C catalyst was introduced into the solution and the resulting mixture was stirred at room temperature for 12 hours using a medium pressure reducing device at a hydrogen gas pressure of 4 atm. After the distillation off of the solvent, the resulting residue was purified by silica gel chromatography (ethyl acetate:hexane=1:1) to thus give 3.77 g (24.0 mmol, 92%) of the intended benzoate (27).

(iii) [1,3',5'-$^{13}C_3$; 1,2',4',6'-$^2H_4$]-Benzaldehyde (28)

The synthesis was carried out with reference to the disclosure of Reference Article (4). There was dissolved 3.77 g (24.0 mmol) of the benzoate (27) in 100 ml of anhydrous THF and then 12 ml of a 1M solution of LiAlD$_4$ in THF was added to the resulting solution at 0° C. After the reaction was continued at room temperature for 30 minutes, 80 ml of a 1N HCl solution was added to the reaction system, the mixture was concentrated under reduced pressure to a volume of about 80 ml, the resulting concentrate was extracted with ethyl acetate (60 ml×3) and then the extract was concentrated under reduced pressure to thus give a benzyl alcohol. This alcohol was dissolved in 200 ml of methylene chloride, 10 g of Molecular Sieves 4A and 3.89 g (36.2 mmol) of PCC were added to the solution at 0° C., the mixture was stirred at 0° C. for 3 hours, packed in a 30ϕ chromatography tube, 12 cm of Celite was added, followed by elution with 1000 ml of diethyl ether and concentration under reduced pressure to thus give 1.9 g (16.7 mmol, 69%) of the title compound: benzaldehyde (28).

(iv) [1,2,3,3',5'-$^{13}C_3$; 1,2',4',6'-$^2H_4$;2-$^{15}N_1$]-benzylidene-azlactone (29)

The synthesis was carried out with reference to the disclosure of Reference Article (5). To 1.50 g (12.3 mmol) of [1,2-$^{13}C_2$;2-$^{15}N_1$]-N-acetyl glycine (28), there were added 1.28 g (11.2 ml) of benzaldehyde, 800 mg (9.75 mmol) of sodium acetate and 3.0 ml of anhydrous acetic acid, and then the resulting mixture was stirred at 115° C. for 2 hours in a nitrogen gas atmosphere. The resulting mixture was concentrated, the resulting crystals were filtered off in an ice bath, washed with cold water, dried under reduced pressure to thus give 1.28 g (6.5 mmol, 58%) of the title compound: benzylidene-azlactone (i).

(v) [1,2,3,3',5'-$^{13}C_5$; 1,2',4',6'-$^2H_4$;2-$^{15}N_1$]-dehydro-N-acetyl-phenylaline methyl ester (30)

The synthesis was carried out with reference to the disclosure of Reference Article (6). There was dissolved 1.28 g (6.5 mmol) of the azlactone (29) in 50 ml of dehydrated MeOH, 500 μl of triethylamine was added to the solution at room temperature and then the resulting mixture was stirred at room temperature for one hour. After the solvent was distilled off under reduced pressure, the residue was loaded on a silica gel column (25×40 mm), followed by elution with 300 ml of ethyl acetate. The solvent was distilled off from the resulting extract to thus give 1.18 g (5.1 mmol, 78%) of the intended dehydro-compound (30).

(vi) [1,2,3,3',5'-$^{13}C_5$; 1,2', 4',6'-$^2H_4$;2-$^{15}N_1$]-N-acetyl-phenylalanine methyl ester (31)

The synthesis was carried out with reference to the disclosure of Reference Article (7). There was dissolved 1.46 g (6.4 mmol) of the dehydro-compound (30) in 20 ml of dehydrated methanol, 35 mg of (S,S)-Et-DuPhos-Rh catalyst was introduced into the solution and the resulting mixture was stirred at room temperature for 16 hours using a medium pressure reducing device at a hydrogen gas pressure of 2 atm. The resulting product was loaded on a silica gel column (20×55 mm), followed by elution with 200 ml of ethyl acetate to thus give 1.40 g (6.0 mmol, 95%) of the intended compound: phenylalanine methyl ester (3).

(vii) [1,2,3,3',5'-$^{13}C_5$; 1,2',4',6'-$^2H_4$;2-$^{15}N_1$]-Phenylalanine (1)

There was dissolved 1.40 g (6.0 mmol) of the phenylalanine methyl ester (31) in 50 ml of a 1N HCl solution and then the resulting solution was stirred at 105° C. for 12 hours. After cooling, the resulting mixture was concentrated and then ion-exchanged using Dowex-50w-X8 to thus give 1.10 mg (5.97 mmol, 99%) of the title compound: phenylalanine (1).

Figure 5:
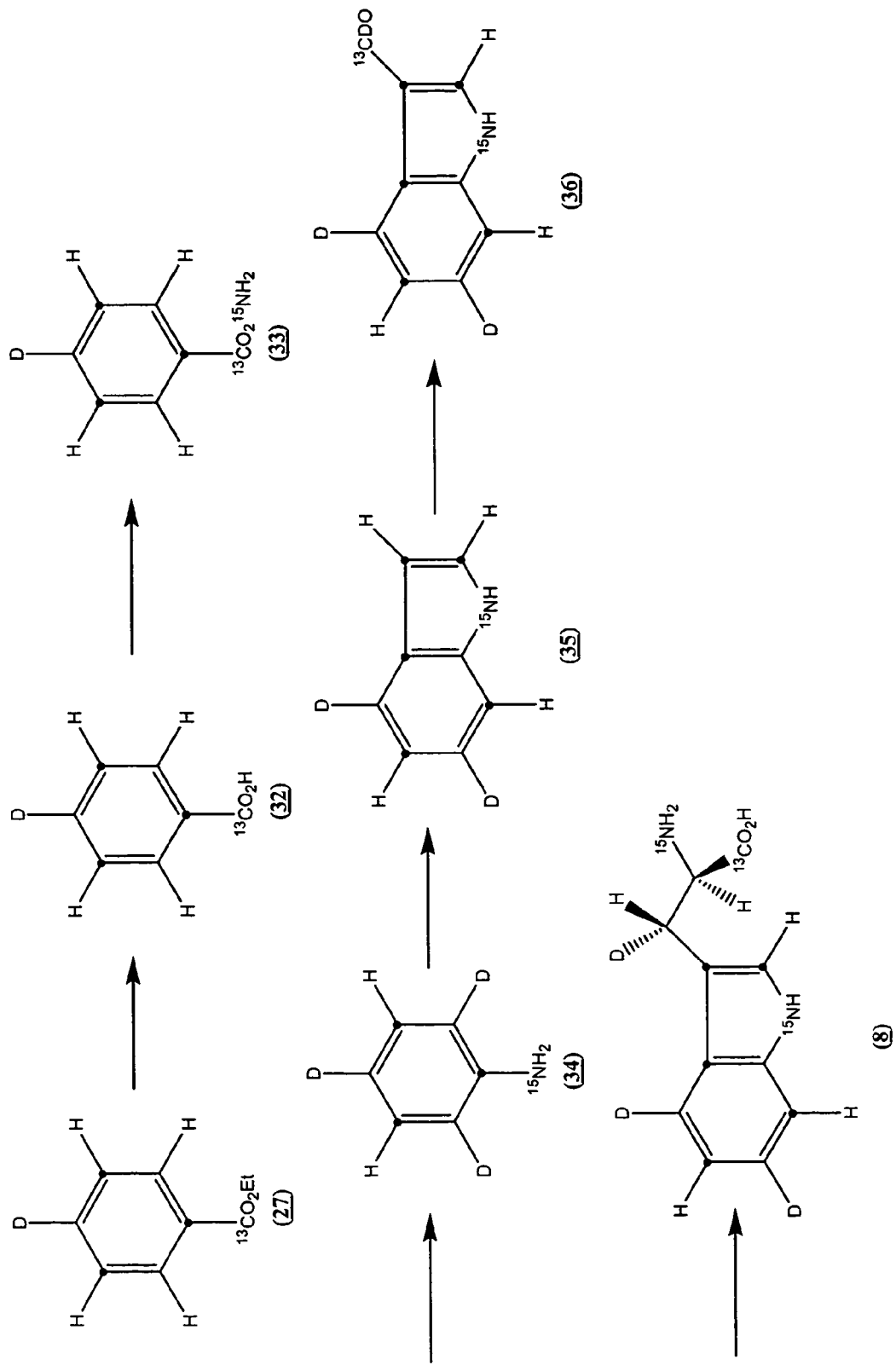
FIG. 5 is a diagram showing the route for synthesizing a stable isotope-labeled tryptophan (8).

Synthesis of Stable Isotope-Labeled Tryptophan (8) (FIG. 5)

(i) Benzoic Acid (32)

To the isotope-labeled benzoate (27), there was added a 2N aqueous solution of sodium hydroxide and then the resulting mixture was stirred at room temperature overnight.

After the addition of hydrochloric acid to the reaction solution, the solution was extracted with methylene chloride. The resulting organic phase was dried and then concentrated.

(ii) Aniline (34)

There was dissolved NaOH (7.2 eq, 7.418 g) in cold water (38 ml) and the resulting solution was cooled to 0° C.

To KMnO4 (15.49 mmol, 2.45 g), there was dropwise added conc. HCl (10 cc) and the chlorine gas thus generated was blown through the NaOH solution. Labeled benzamide (33) (2.63 g, 20.76 mmol) was added to the solution, the temperature of the mixture was raised up to 100° C. and then the mixture was stirred for one hour. The reaction solution was extracted with ether, the organic phase thus obtained was dried over $Na_2SO_4$ and then filtered. Dry HCl gas was blown through the ether solution and the resulting aniline hydrochloride was filtered off. deuterium oxide was added to the resulting crystals, the mixture was concentrated, then deuterium oxide (60 ml) was additionally added to the resulting concentrate and subsequently, the mixture was stirred at 120° C. for 2 days using a pressure tube. The reaction solution was cooled down to 0° C., followed by addition of a 2N NaOH solution (20 ml), extraction with methylene chloride, drying of the resulting organic phase and concentration of the phase to thus give aniline (34), in a yield of 16.8 mmol.

(iii) Indole (35)

The synthesis was carried out with reference to the disclosure of Reference Article 11. There was dissolved aniline (34) (16.8 mmol) in methylene chloride, the resulting solution was cooled to −70° C., a solution (8 ml) of separately synthesized BuOCl (16.8 mmol) in methylene chloride was dropwise added to the cooled solution and then the mixture was stirred at −70° C. for 15 minutes. To the reaction solution, there was dropwise added a solution (8 ml) of separately synthesized $MeSCH_2CO_2Et$ (16.8 mmol) in methylene chloride over not less than one hour and the mixture was further stirred for 2 hours. To the resulting reaction solution, there was dropwise added a solution (8 ml) of TEA (16.8 mmol) in methylene chloride over not less than 30 minutes, the mixture was stirred for 15 minutes at that temperature and then the temperature thereof was raised up to room temperature. To the mixture, there was added 10 ml of water, the mixture was then stirred for 15 minutes, followed by concentration, addition of ether (20 ml) and a 2M HCl (13 ml), extraction with ether, drying of the extract and the subsequent concentration thereof. The resulting compound (4.25 mmol) was dissolved in HMPA (5 ml) and an LR reagent (2.1 mmol) was added in an argon atmosphere. After the post-treatment, Ra—Ni (4-spoonful) and MeOH (60 ml) were added to the mixture and the latter was refluxed with heating for one hour. The Raney-Ni catalyst was removed from the reaction system through decantation, the solution was concentrated, followed by drying of the concentrate and purification by column chromatography (3 cm) to thus give indole (35) in a yield of 3.76 mmol (88%).

(iv) Indole-3-Carboxyaldehyde (36)

[a-$^2H$; a-$^{13}C$]-DMF (7.52 mmol) was dissolved in THF (4 ml), phosphorus oxychloride (3.76 mmol) was added to the resulting solution with stirring in an ice bath, a solution (50 ml) of the indole (35) (3.76 mmol) in THF was further added to the resulting mixture, followed by stirring of the mixture at room temperature for 3 hours. After the confirmation of the completion of the reaction using the TLC method, the reaction system was cooled in an ice bath, water (30 ml) and 2M NaOH aqueous solution were added till an alkaline solution was obtained, the resulting alkaline solution was extracted with methylene chloride-methanol (95:5) mixed solvent (100 ml×3), the extract was washed with a saturated sodium chloride aqueous solution (100 ml×3) and then dried over anhydrous magnesium sulfate. After filtration under reduced pressure, the solvent was distilled off from the filtrate and the resulting residue was purified by silica gel chromatography (developing solvent: methylene chloride/methanol=94/6) to thus give an aldehyde (36) in a yield of 2.68 mmol (71%).

(v) Tryptophane (8)

To [12-$^{13}C_2$;2-$^{15}N$]-N-acetyl glycine (3.4 mmol), there were added indole-3-carboxy-aldehyde (35) (2.86 mmol), sodium acetate (5.15 mmol) and anhydrous acetic acid (20 mmol) and then the resulting mixture was stirred at 120° C. for 8 hours in an argon gas atmosphere. The resulting mixture was cooled in an ice bath, the resulting crystals were filtered off, washed with a small amount of cold water, then dried under reduced pressure, the resulting crystals were added to a 0.5M aqueous sodium carbonate solution (20 ml) and the mixture was refluxed at 140° C. for 4 hours. After cooling in an ice bath, the insolubles were removed through the filtration under reduced pressure using celite, cold conc. HCl was added thereto till an acidic solution was obtained, the crystals were filtered off, washed with cold water and then dried under reduced pressure to thus give N-acetyl-dehydro-tryptophan. This N-acetyl-dehydro-tryptophan was dissolved in ethanol (30 ml), PtO$_2$ (0.05 g) was added to the solution, and the compound was then hydrogenated at room temperature and ordinary pressure (1 atm). After 10 days, the disappearance of the starting materials was confirmed by the $^1$H-NMR spectrometry and the catalyst used was then removed by the filtration under reduced pressure using celite, thereafter the solvent was distilled off and the resulting residue was dried under reduced pressure to thus give N-acetyl tryptophan. The resulting N-acetyl tryptophan was dissolved in a 1M aqueous solution of sodium hydroxide (50 ml), a 1M HCl solution was then added to the solution and anhydrous cobalt chloride (10 mg) was added thereto. To the resulting mixture, there was carefully added a 1M aqueous solution of sodium hydroxide or a 1M HCl solution to adjust the pH value thereof to 8, acylase (150 mg) originated from filamentous fungi and the mixture was stirred at 37° C. for 3 days. The catalyst used was then removed by the filtration under reduced pressure using Celite, thereafter the water was distilled off, a 2M hydrochloric acid solution was added to the filtrate till the pH thereof reached 1 to thus crystallize the acetyl derivative and the crystals were filtered off. The filtrate was concentrated and then ion-exchanged using Amberlite CG50 to thus give tryptophan (8) (0.315 g, 1.529 mmol) and N-acetyl-D-tryptophan.

Figure 6:
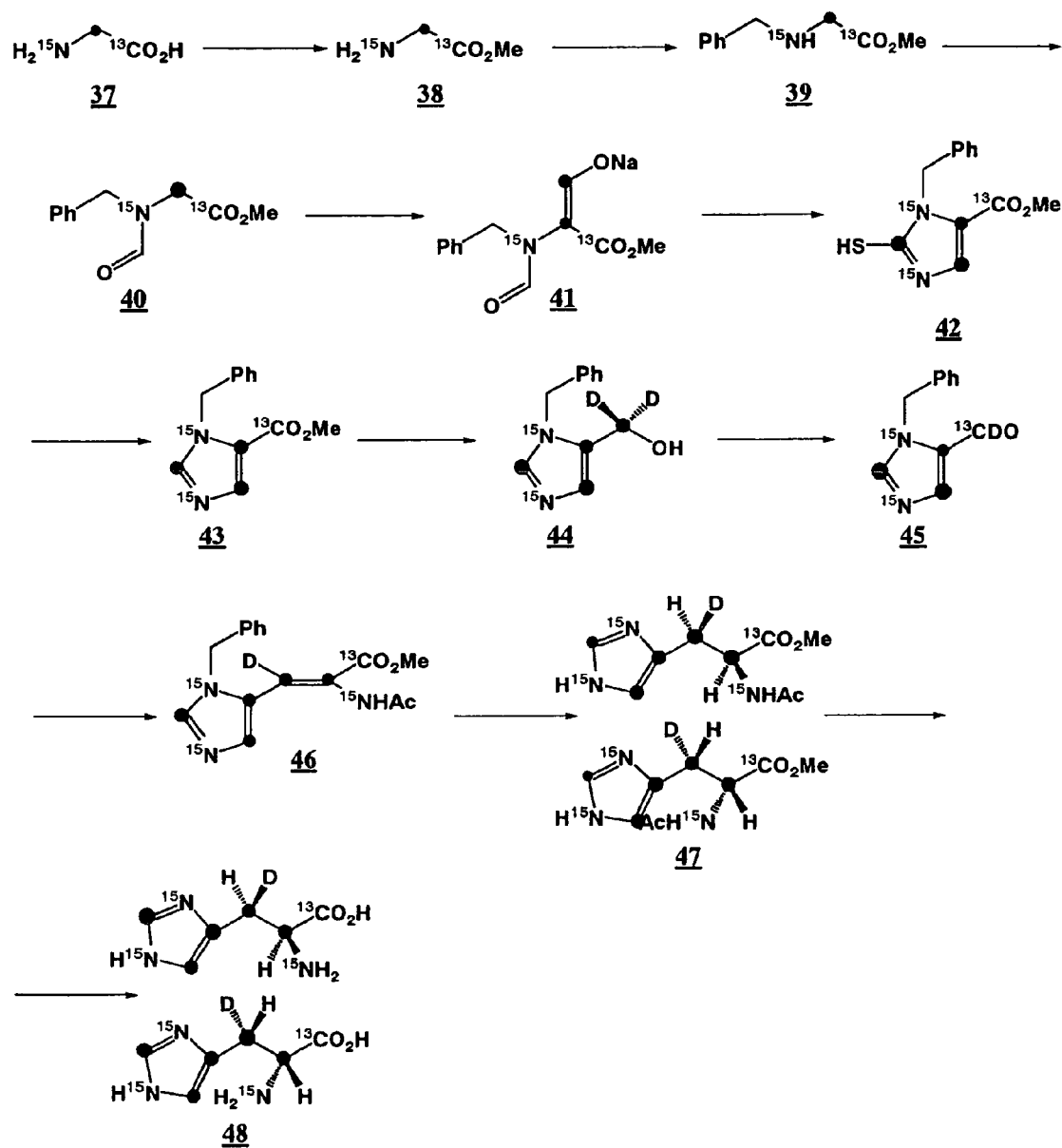
FIG. 6 is a diagram showing the route for synthesizing a stable isotope-labeled histidine (48).

Synthesis of Stable Isotope-Labeled Histidine (48)
(FIG. 6)

(i) Glycine (3) (7.50 g, 100 mmol) was suspended in methanol, SoCl$_2$ (11.9 g, 100 mmol) was dropwise added to the suspension and the latter was refluxed for about one hour. Methanol was added and then the resulting mixture was concentrated. These two operations were repeated several times to thus almost quantitatively obtain the crystals of the hydrochloride of a compound (38).

(ii) PhCH$_2$Br (17.1 g, 100 mmol) was dissolved in TBF (100 ml) and Et$_3$N (20.2 g, 200 mmol) was added with sufficient stirring. After a short time, the substrate (38) was added to the foregoing mixture and stirred at room temperature overnight. After the completion of the reaction, the Et$_3$N—HBr salt was removed through filtration and the filtrate was concentrated to give an intended product (39) (15.1 g, 84.4 mmol, 84.4%).

(iii) The substrate (39) was dissolved in formic acid (45 ml) under ice cooling and anhydrous acetic acid (45 ml) was added to the resulting solution in small portions. After heating at 100° C. for about 1 to 2 hours, the solution was concentrated to evaporate the formic acid and acetic acid. Methylene chloride was added for the purpose of extraction, the resulting organic phase was washed with a saturated NaHCO$_3$ aqueous solution 4 times, then wit water and a saturated NaCl aqueous solution. The organic phase was dried over Na$_2$SO$_4$ and then concentrated. The concentrate was purified by a silica gel column (developing solvent:hexane/ethyl acetate=2/1) to give an intended product (40) (8.12 g, 39.1 mmol, 46.3%).

(iv) To the substrate (40) (17.17 g, 81.7 mmol), there was added 12.4 g (203.2 mmol) of H$^{13}$COMe under an N$_2$ gas flow, the resulting mixture was stirred on an ice bath, NaOMe (6.61 g, 122.5 mmol) and dry toluene (40 ml) were added, the resulting mixture was stirred at a temperature of not more than 15° C. for about 2 hours and then allowed to stand at 0° C. overnight. To the reaction mixture, there was added dry ether, crystals of an Na salt (41) precipitated out were recovered through filtration and then dried (3.51 g, 12.9 mmol, 33.0%).

(v) To the substrate (41), there were added a 50% MeOH. solution (70 ml) and a 12N HCl solution (13.6 ml), the resulting mixture was stirred at room temperature overnight, KS$^{13}$C$^{15}$N (7.43 g, 76.5 mmol) was added to the mixture and the mixture was then stirred at 80° C. for 4 hours. The crystals precipitated out were recovered through filtration and then dried to give an intended product (42) (18.5 g, 70.9 mmol, 87%).

(vi) There was dissolved the substrate (42) (18.5 g, 70.9 mmol) in dry EtOH (70 ml), Raney nickel (about 20 g) was suspended in dry EtOH and the suspension was added to the foregoing solution in small portions. The resulting mixture was heated at 100° C. for about 1 to 2 hours. The reaction system was filtered through a Celite layer and the filtrate was concentrated. The residue was purified by a silica gel column (developing solvent:hexane/ethyl acetate=1/1) to thus give an intended product (43) (8.12 g, 39.1 mmol, yield 56.6%).

(vii) To a 3-necked flask, there were added LiAlD$_4$ (0.41 g) and dry THF (50 ml) and then the substrate 43 (2.18 g, 9.8 mmol) was dissolved in dry THF (15 ml) and the resulting solution was added to the flask. The mixture was stirred at room temperature for 3 hours and the reaction was then stopped by the addition of water (10 ml). To the reaction system, there was added a 6N HCl solution to adjust the pH thereof to 8 to 9, the mixture was extracted with methylene chloride, and the resulting organic phase was washed with a saturated common salt solution. After drying the organic phase over Na$_2$SO$_4$, the phase was concentrated to thus give an intended product (44) (0.65 g, 3.3 mmol, yield 34%).

(viii) The substrate (44) (0.65 g, 3.3 mmol) was dissolved in chloroform (15 ml), followed by addition of MnO$_2$ (2 g) to the solution and stirring of the mixture at room temperature for 2 days. The mixture was filtered through a Celite layer and the resulting filtrate was concentrated. The residue thus obtained was purified by a silica gel column (developing solvent:chloroform/methanol=9/1) to thus give an intended product (45) (0.61 g, 3.1 mmol, yield 96.0%).

(ix) Uniformly labeled phosphoryl glycine (0.4988 g, 2.06 mmol) was dissolved in methylene chloride (5 ml), DBU (0.487 ml, 3.17 mmol) was added to the solution in an ice bath, the resulting mixture was stirred at room temperature for 30 minutes, a solution prepared by dissolving the substrate (45) (0.767 g, 3.17 mmol) in methylene chloride (5 ml) was added to the mixture and the mixture was stirred at room temperature overnight. After the concentration of the mixture, the residue obtained was dissolved in ethyl acetate, the resulting solution was washed with a saturated $NH_4Cl$ aqueous solution, dried over $Na_2SO_4$ and then concentrated to thus give an intended product (46) (0.625 g, 2.06 mmol, yield 65.0%).

(x) The substrate (46) (0.312 g, 1.03 mmol) was dissolved in methylene chloride (5 ml) and methanol (5 ml), Pd/C (0.3 g) was added to the solution and the substrate was hydrogenated at room temperature and at a pressure of 5 atm. After 3 days, the reaction system was filtered through a Celite layer and the resulting filtrate was concentrated. The residue thus obtained was purified by a silica gel column (developing solvent:chloroform/methanol=9/1) to thus give an intended product (47) (0.205 g, 0.957 mmol, yield 92.9%).

(xi) To the substrate (47) (0.205 g, 0.957 mmol), there was added a 1N HCl solution (10 ml), the mixture was refluxed at 100° C. overnight and then concentrated to thus give hydrochloride of histidine (48) (0.0845 g).

Figure 11:
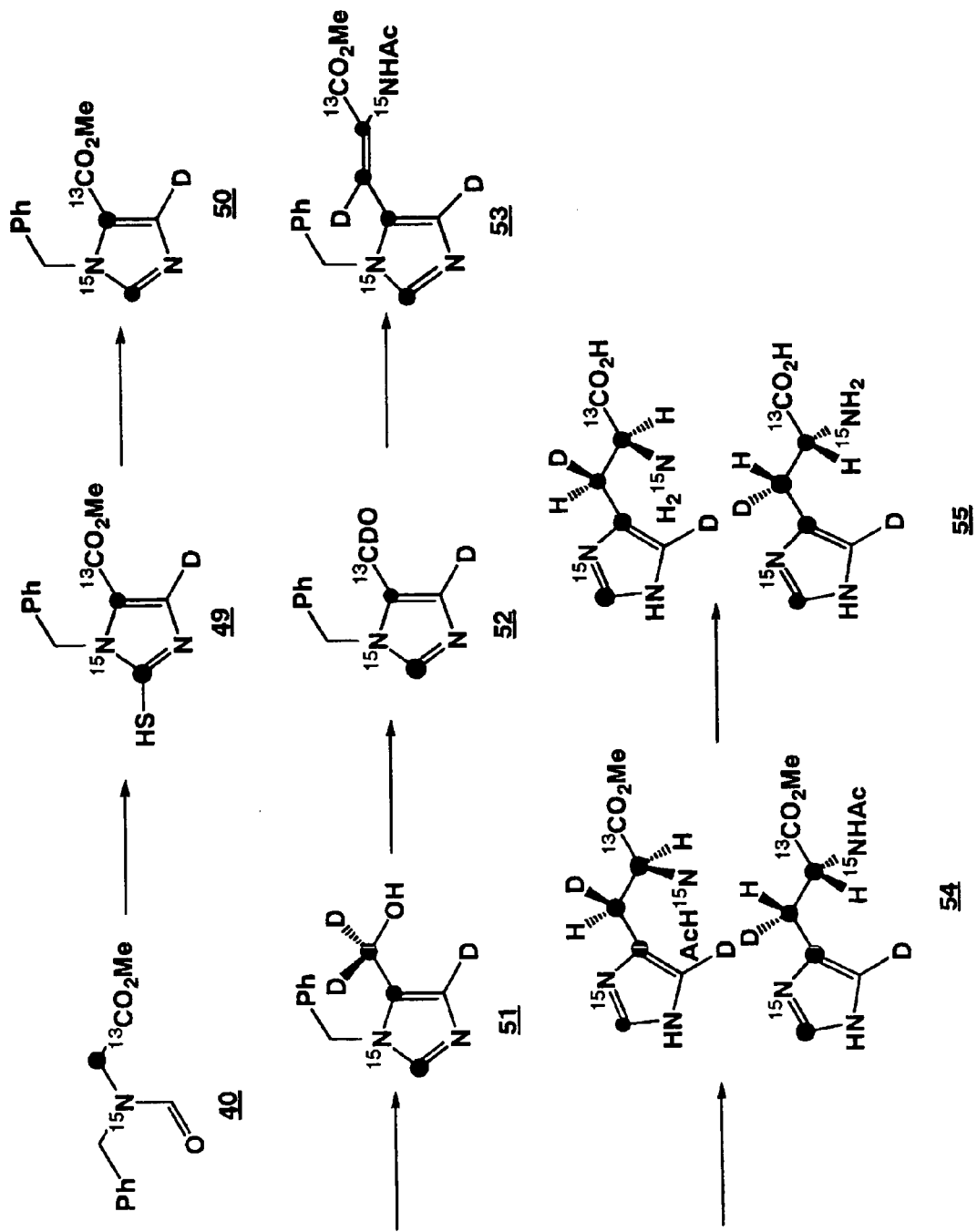
FIG. 11 is a diagram showing the route for synthesizing a stable isotope-labeled histidine (55).
Figure 12:
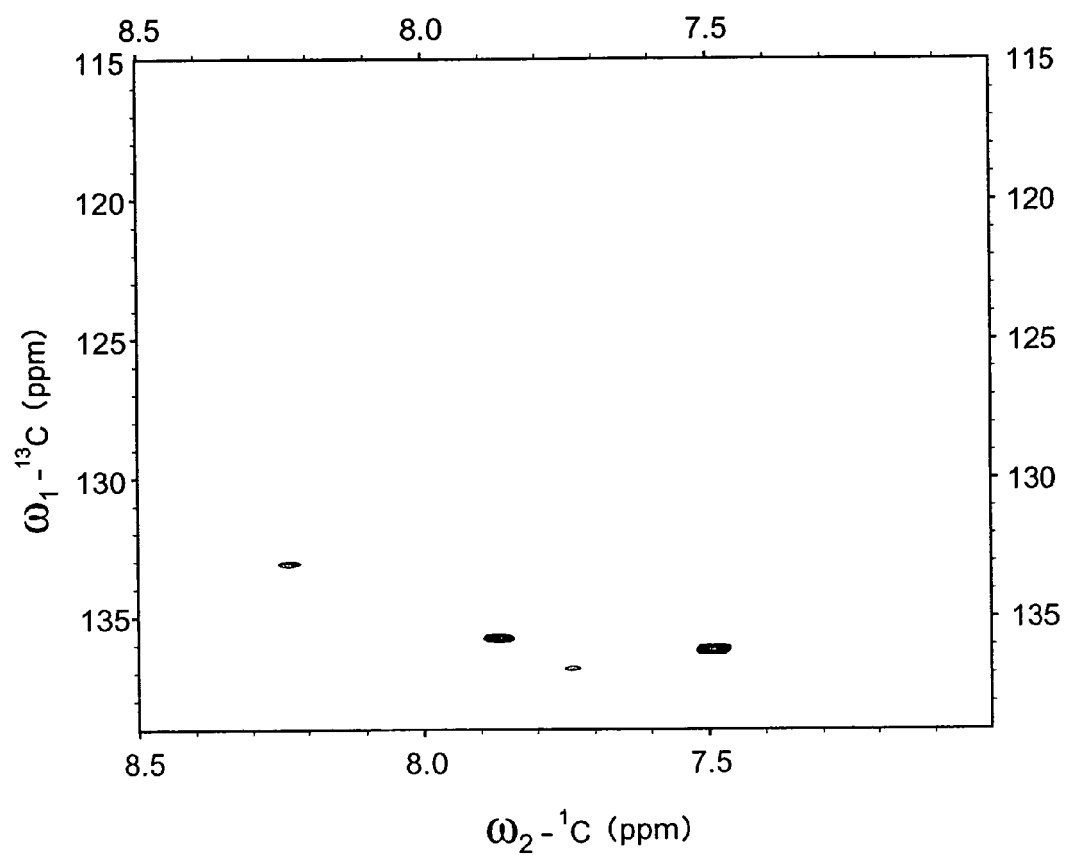
FIG. 12 shows $^1$H-$^{13}$CHSQC spectra of a protein (MBP: Maltose Binding Protein) which comprises the stable isotope-labeled histidine (55) incorporated into the same.
Figure 13:
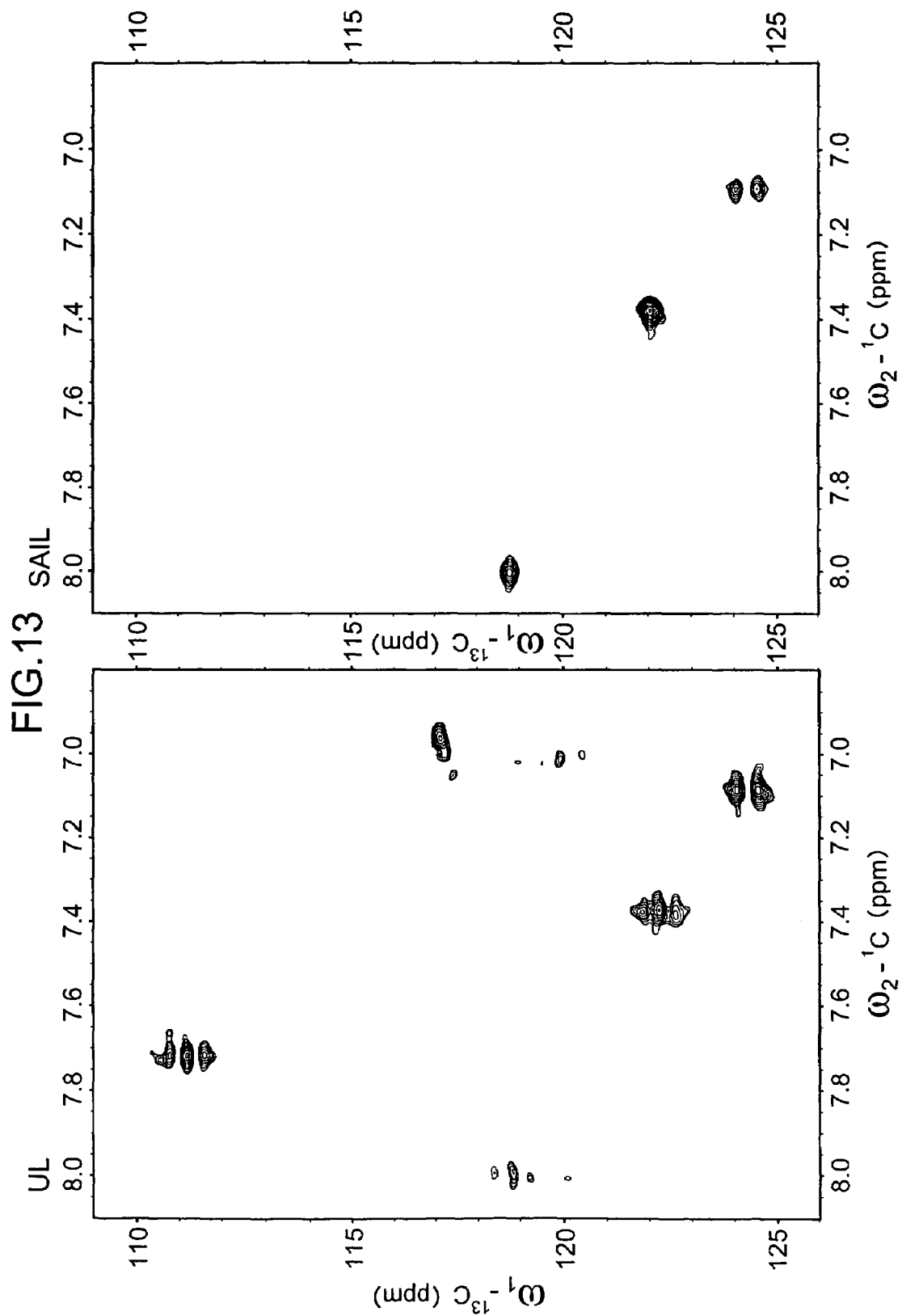
FIG. 13 shows $^1$H-$^{13}$CHSQC spectra of a protein (EPPI) which comprises the stable isotope-labeled tryptophan (8) incorporated into the same.

Synthesis of Stable Isotope-Labeled Histidine (55)
(FIG. 11)

According to the synthesis route as shown in FIG. 11, stable isotope-labeled histidine (55) was prepared using, as isotope-labeled raw materials, [ul-$^{13}$C;$^{15}$N]-Gly, $^2HCO_2Me$ and $KS^{13}CN$, while making use of the foregoing synthesis method.

(i) T the substrate (40) (7.854 g, 37.4 mmol), there was added $^2HCO_2Me$ (10.87 g, 178 mmol) under an $N_2$ gas flow, the resulting mixture was stirred on an ice bath, NaOMe (5.710 g, 65.7 mmol) and dry toluene (44 ml) were added. The resulting mixture was stirred at a temperature of not more than 15° C. for about 2 hours and then allowed to stand at 0° C. overnight. The mixture was then concentrated without any pre-treatment, a 50% MeOH solution (70 ml) and a 12N HCl solution (13.6 ml) were added thereto and the resulting mixture was stirred at room temperature overnight. $KS^{13}CN$ (3.318 g, 33.8 mmol) was added to the mixture, and the mixture was stirred at 80° C. for 4 hours. The crystals precipitated out were recovered through filtration and then dried (5.065 g, 20.0 mmol, 41%).

(ii) The substrate 49 (3.859 g, 15.3 mmol) was dissolved in dry EtOH (70 ml), a suspension prepared by dispersing Raney nickel (about 20 g) in dry EtOH was added to the solution in small portions. The mixture was heated at 100° C. for about 1 to 2 hours. It was filtered through a Celite layer and the filtrate was concentrated. The residue obtained was purified by a silica gel column (developing solvent:hexane/ethyl acetate=1/1) to thus give an intended product 2 (2.312 g, 10.9 mmol, 71%).

(iii) To a 3-necked flask, there were added $LiAlD_4$ (0.458 g, 10.9 mmol) and dry THF (100 ml) and a solution prepared by dissolving the substrate 50 (2.3 g, 10.9 mmol) in dry THF (15 ml) was then added to the flask. The resulting mixture was stirred at room temperature for 3 hours and the reaction was then stopped by the addition of water (10 ml). To the reaction system, there was added a 6N HCl solution to adjust the pH thereof to 8 to 9, the mixture was extracted with methylene chloride, and the resulting organic phase was washed with a saturated common salt solution. After drying the organic phase over $Na_2SO_4$, the phase was concentrated to thus give an intended product 51 (1.878 g, 9.62 mmol, 89%).

(iv) The substrate 51 (1.878 g, 9.62 mmol) was dissolved in chloroform (45 ml), $MnO_2$ (6 g) was added to the solution and the resulting mixture was stirred at room temperature for 2 days. The mixture was filtered through a Celite layer and the resulting filtrate was concentrated. The residue thus obtained was purified by a silica gel column (developing solvent:chloroform/methanol=9/1) to thus give an intended product 52 (1.703 g, 8.86 mmol, 92%).

(v) Uniformly labeled phosphoryl glycine (2.150 g, 8.87 mmol) was dissolved in methylene chloride (5 ml), DBU (1.350 ml, 8.87 mmol) was added to the solution in an ice bath, the resulting mixture was stirred at room temperature for 30 minutes, a solution prepared by dissolving the substrate 52 (1.703 g, 8.86 mmol) in methylene chloride (5 ml) was added to the mixture and the mixture was stirred at room temperature overnight. After the concentration of the mixture, the residue obtained was dissolved in ethyl acetate, the resulting solution was washed with a saturated $NH_4Cl$ aqueous solution, the resulting organic phase was dried over $Na_2SO_4$ and the phase was then concentrated to thus give an intended product 53 (1.042 g, 3.38 mmol, 38%).

(vi) The substrate 53 (0.398 g, 1.29 mmol) was dissolved in methylene chloride (15 ml) and methanol (15 ml), Pd/C (0.7 g) was added to the solution and the substrate was hydrogenated at room temperature and at a pressure of 5 atm. After 3 days, the reaction system was filtered through a Celite layer and the resulting filtrate was concentrated to thus give an intended product 54 (0.247 g, 1.20 mmol, 93%).

(vii) To the substrate 54 (0.247 g, 1.20 mmol), there was added a 1N HCl solution (10 ml), the mixture was refluxed at 100° C. overnight and then concentrated to thus give hydrochloride of histidine 55 (0.240 g).

EXAMPLE 2

NMR Measurement and Analysis

As has been described in the foregoing section entitled "Background Art", the greater part of the globular proteins have hydrophobic core portions each comprising aromatic amino acids such as Phe, Tyr and Trp and amino acids each carrying an alkyl side chain such as Leu, Val and Ile. For this reason, if determining the three-dimensional structure of a protein by the NMR spectrometry, it is necessary to experimentally determine the distance-limitation information required for recognizing the real and mutual relation between the relative positions of these amino acids. In general, such distance-limitation can be obtained by experimentally determining the nuclear Overhauser effect (NOE) for the NMR signal of each hydrogen nucleus (proton) while making use of the fact that the 1H-1H dipole interaction is proportional to (spatial distance)$^{-3}$. In short, the present invention permits the measurement of NOE for high molecular weight proteins, which have not conventionally been considered as subjects for the structural analysis according to the NMR technique because of the experimental limitation in the determination of NOE, in particular, NOE for high molecular weight proteins each having protons ascribed to aromatic amino acids indispensable to the experiments for the determination of structures, in a high sensitivity and in a high precision. Microorganisms or other cells are cultivated using a culture medium which comprises the novel and stable isotope-labeled aromatic amino acids according to the present invention to thus specifically label the amino acid residues present in the proteins produced by these microorganisms or cells or proteins present therein attributable to extraneous genes incorporated into the same. To avoid any dilution of the labeled amino acids during the cultivation and to increase the yield of the protein with respect to the labeled amino acids, it is preferred to use the technique or so-called cell-free protein-expression system in which protein-synthesis factors are extracted from living cells and extraneous genes are expressed, rather than the cultivation of any living cell. The experimental process for the determination of NOE will hereunder be briefly described for the purpose of illustrating how the protein samples comprising the novel labeled aromatic amino acids thus obtained, which are incorporated therein, are advantageous in the NMR analysis as compared with the conventional samples uniformly labeled with isotopes (uniform isotope-labeled samples).

The high molecular weight protein in general includes a plurality of aromatic amino acids and accordingly, a large number of signals ascribed to, for instance, Phe, Tyr, His and Prp appear in the NMR spectral region for the aromatic rings in the condition superimposed on each other and accordingly, it would be quite difficult to carry out "the sequence-assignment of signals" which can assign each signal to a specific site on the aromatic ring, or which can assign each signal to a specific amino acid residue in an amino acid sequence. For this reason, it would be essential to the correct sequence-assignment of signals to prepare a uniform $^{13}$C-labeled sample in which all of the naturally occurring carbon atoms ($^{12}$C) on a protein are completely replaced with $^{13}$C and to use the multi-nuclear multi-dimensional NMR technique wherein the $^{13}$C-observation axis is added to the $^1$H-observation axis. In these existing methods (those disclosed in, for instance, Reference Articles: a) Rueterjans et al., b) Bax et al., c) Kay et al.), however, it takes a long measurement time on the order of several days to about one week for the structural analysis of even a relatively low molecular weight protein and it is quite rare that specific signals are observed for all of the aromatic amino acid residues included therein and they can completely be ascribed to the aromatic amino acid residues. The novel labeled aromatic amino acids synthesized in the present invention are so designed that the spin-spin coupling constants observed between remote $^{13}$C—$^{13}$C and remote $^{13}$C—$^1$H which can provide a sufficiently large size for the magnetization-movement can be used for the signal-assignment, when the magnetization-movement through the spin-spin coupling between the directly bonded carbon atoms is not efficiently induced due to the complexity of the spin system in the aromatic ring portion. In addition, when the structure is determined using the NOE observed between the protons on an aromatic ring and the neighboring amino acid residue, it is not always essential to the determination of structures to obtain or use the NOE information for all of the protons on the aromatic ring and rather NOE information sufficient for the structure-determination is available if at least one hydrogen nucleus remains on each aromatic ring. Therefore, when explaining this while taking Phe by way of example, only C ε and C γ are labeled with $^{13}$C for the labeled derivative of type (1) and only C γ-C ζ are labeled with $^{13}$C for the labeled derivative of type (2) and accordingly, the use thereof may have such an advantage that the usual HSQC can be used instead of the constant time HSQC for the removal of the directly bonded $^{13}$C—$^{13}$C spin-spin coupling (FIG. 5).

Figure 7:
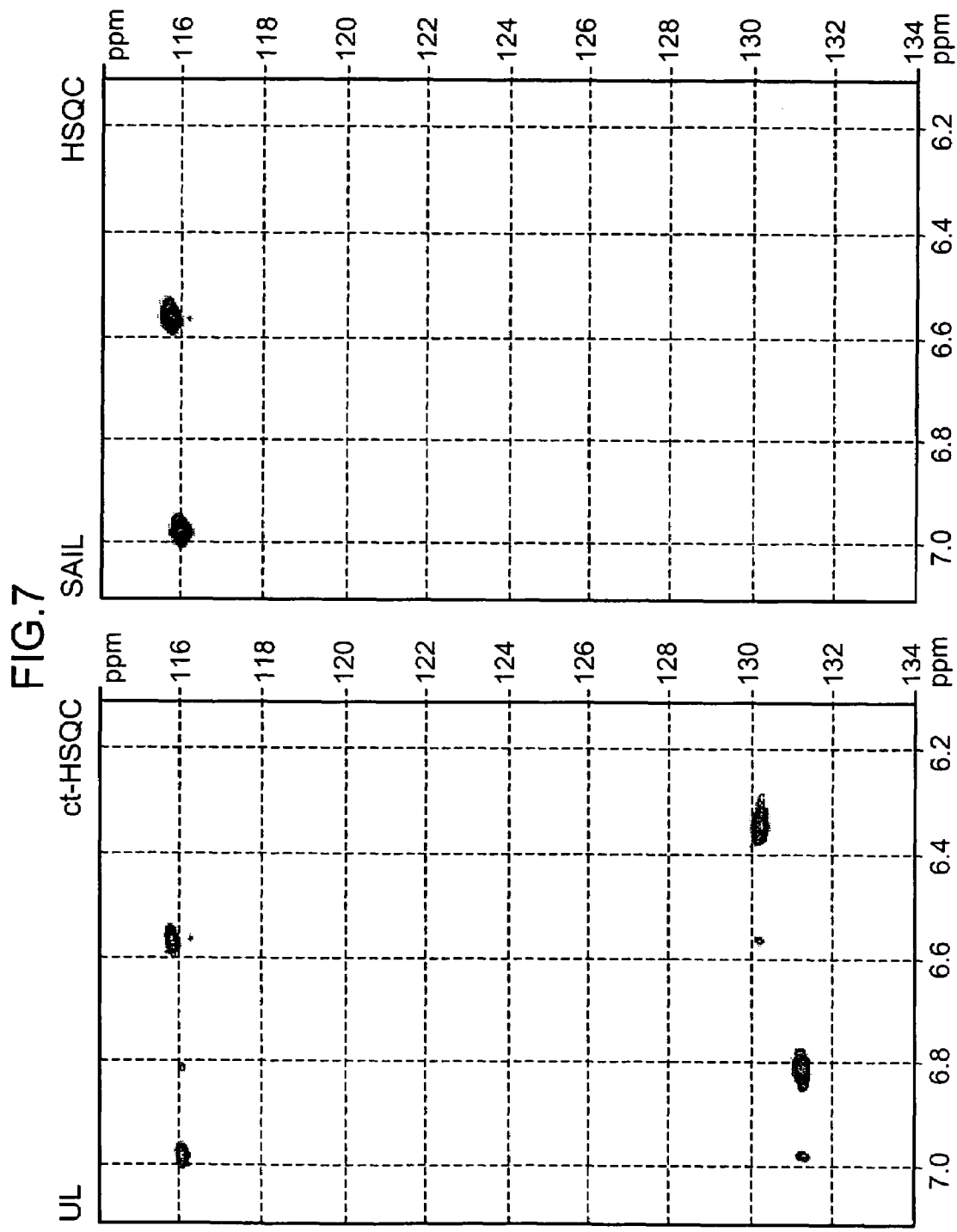
FIG. 7. shows 1H-$^{13}$C(ct-)HSQC spectra of Tyr-selectively labeled calmoduhin.
Figure 8:
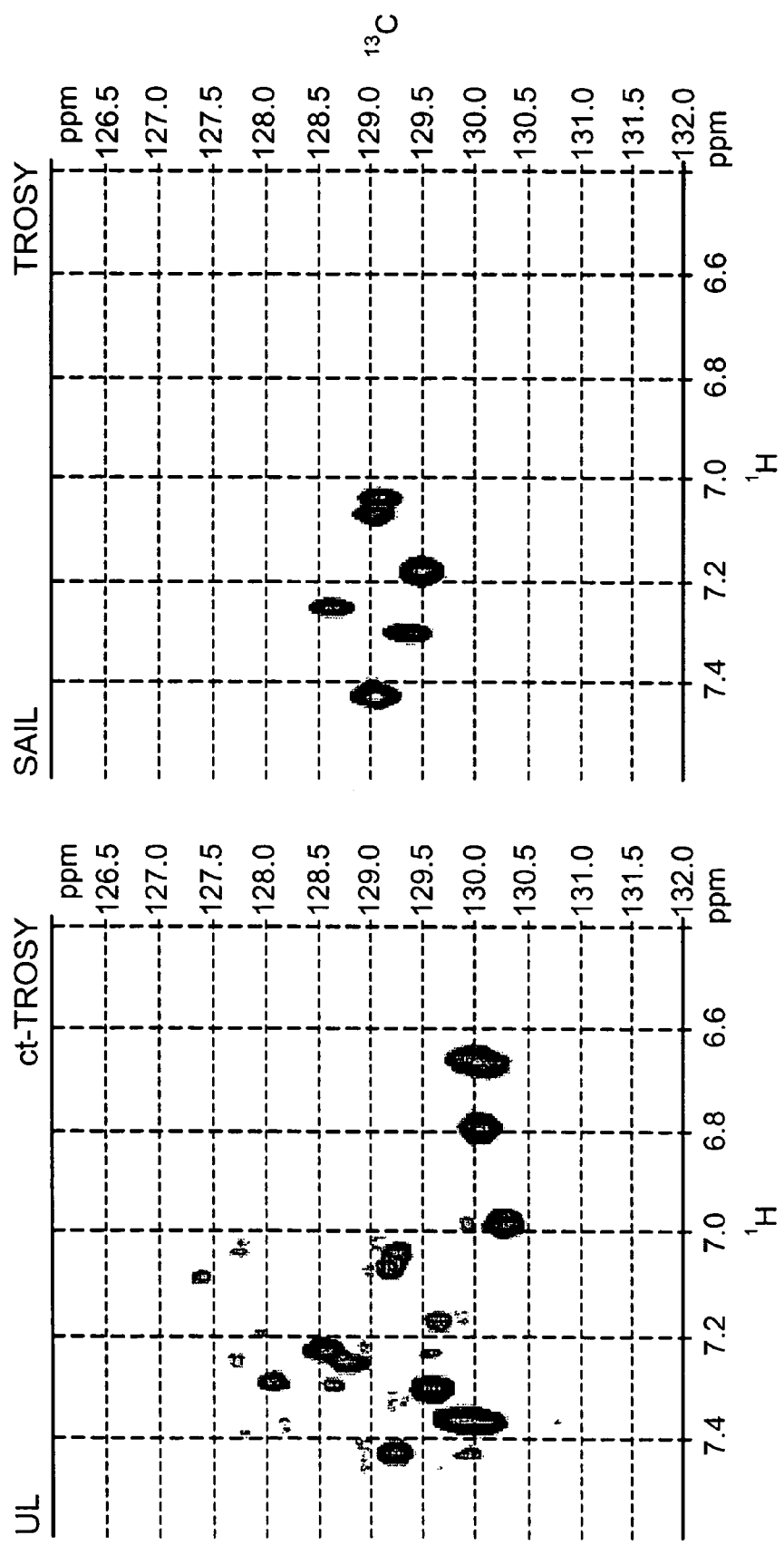
FIG. 8. shows 1H-$^{13}$C(ct-)TROSY spectra of Phe-selectively labeled calmodulin.
Figure 9:
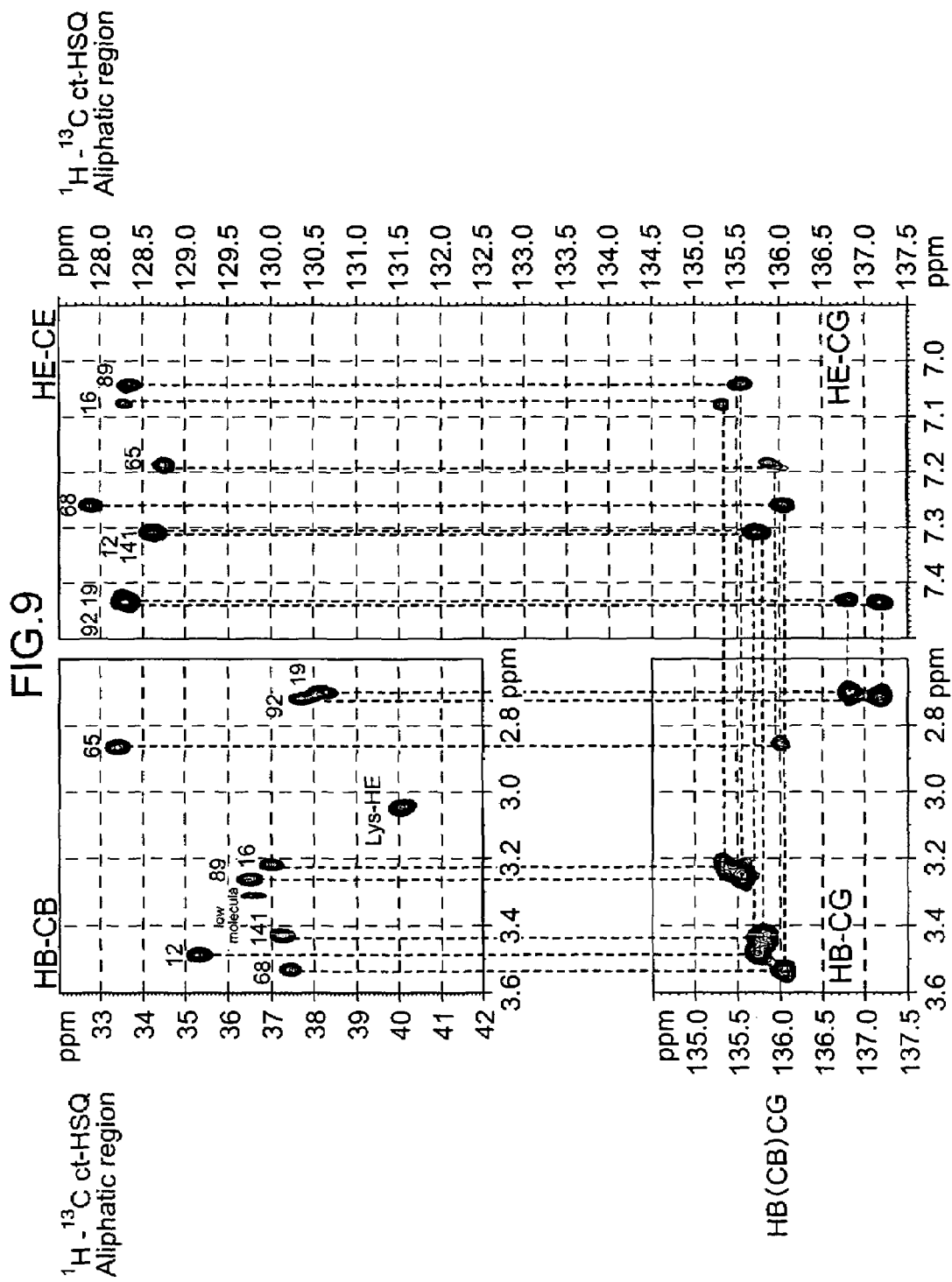
FIG. 9 shows the steps for assigning H ε proton of the Phe-selectively labeled calmodulin.
Figure 10A:
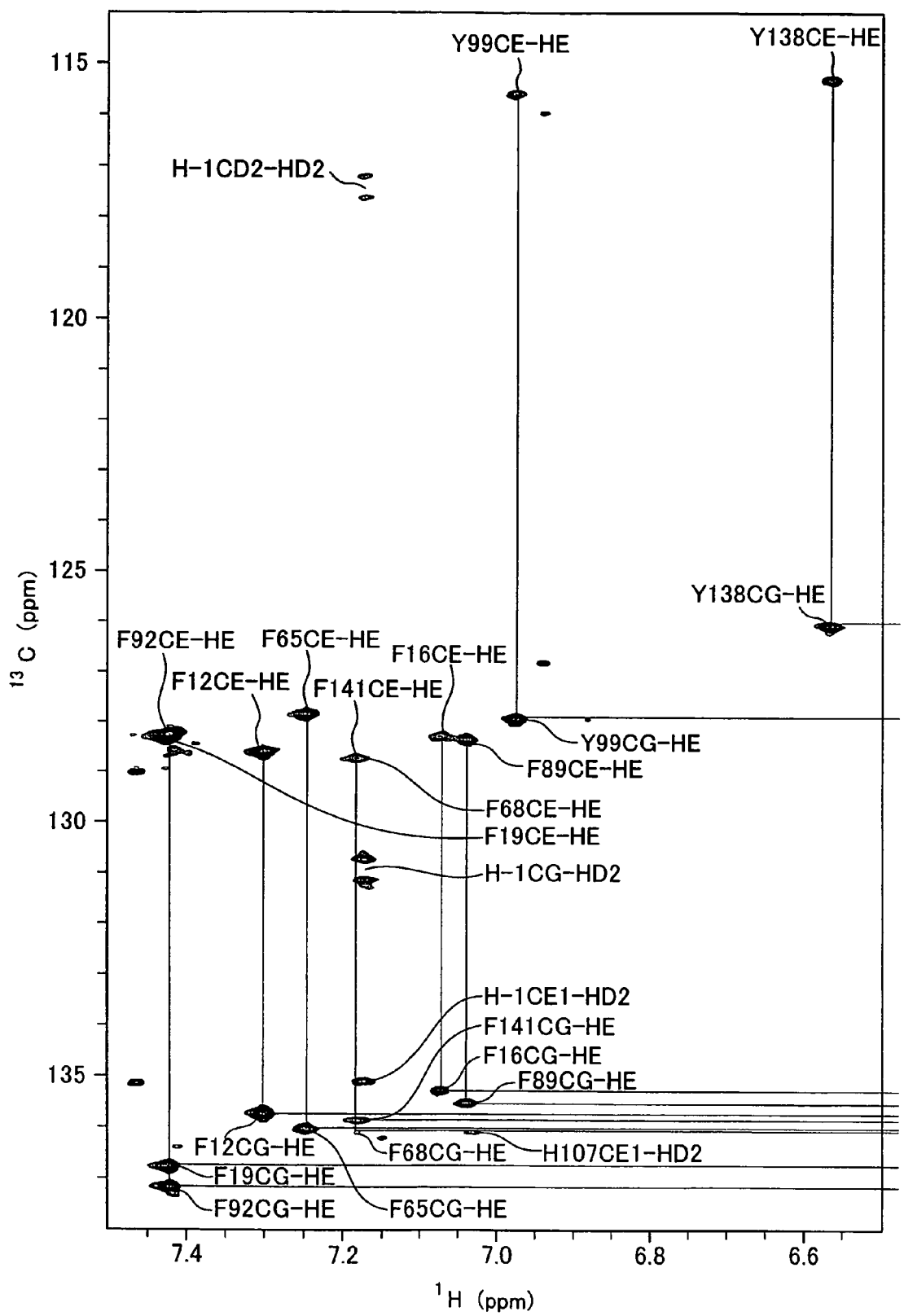
FIG. 10 shows the steps for assigning H ε proton of the Tyr- and Phe-selectively labeled calmodulin.
Figure 10B:
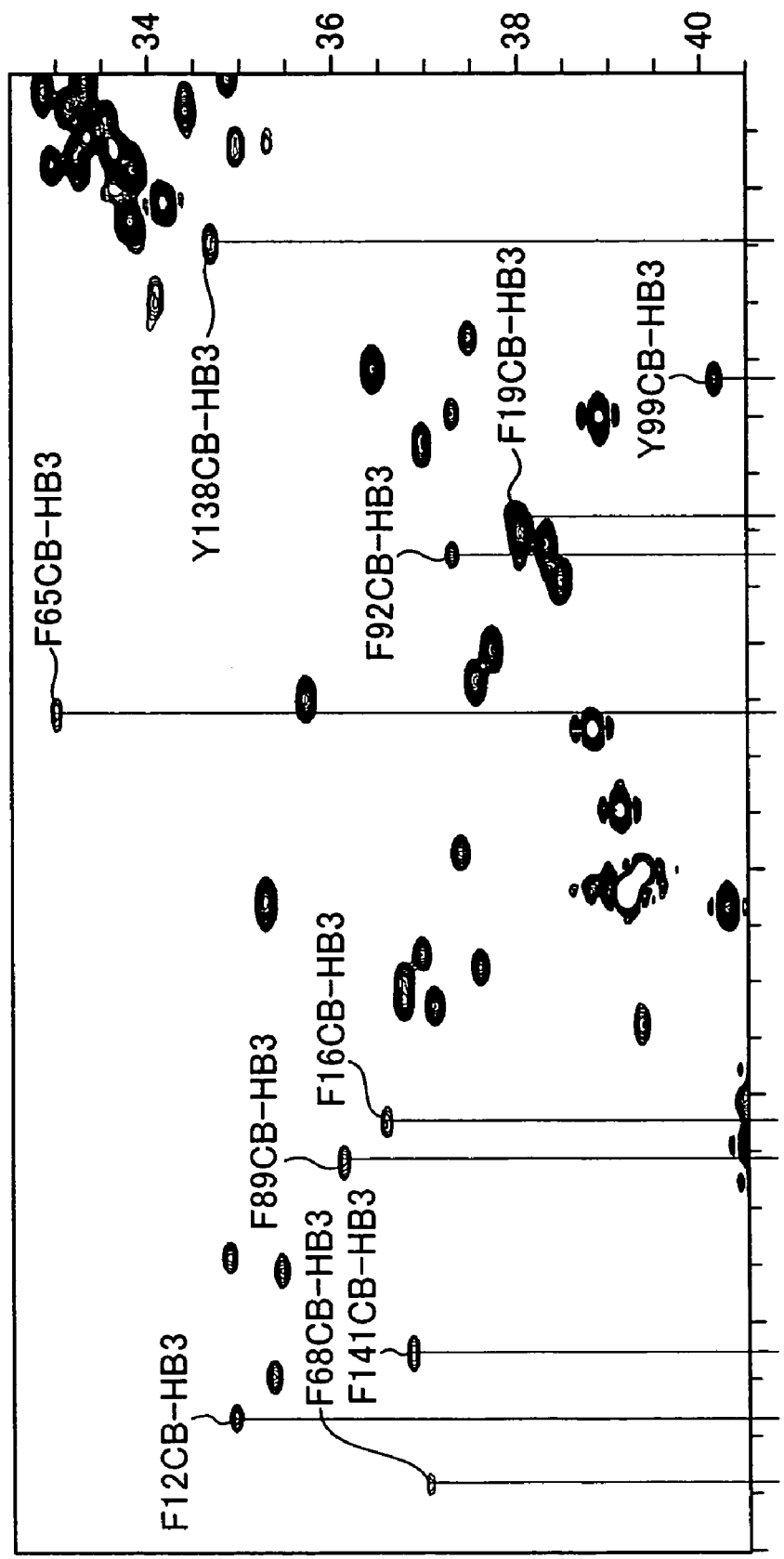
Figure 10C:
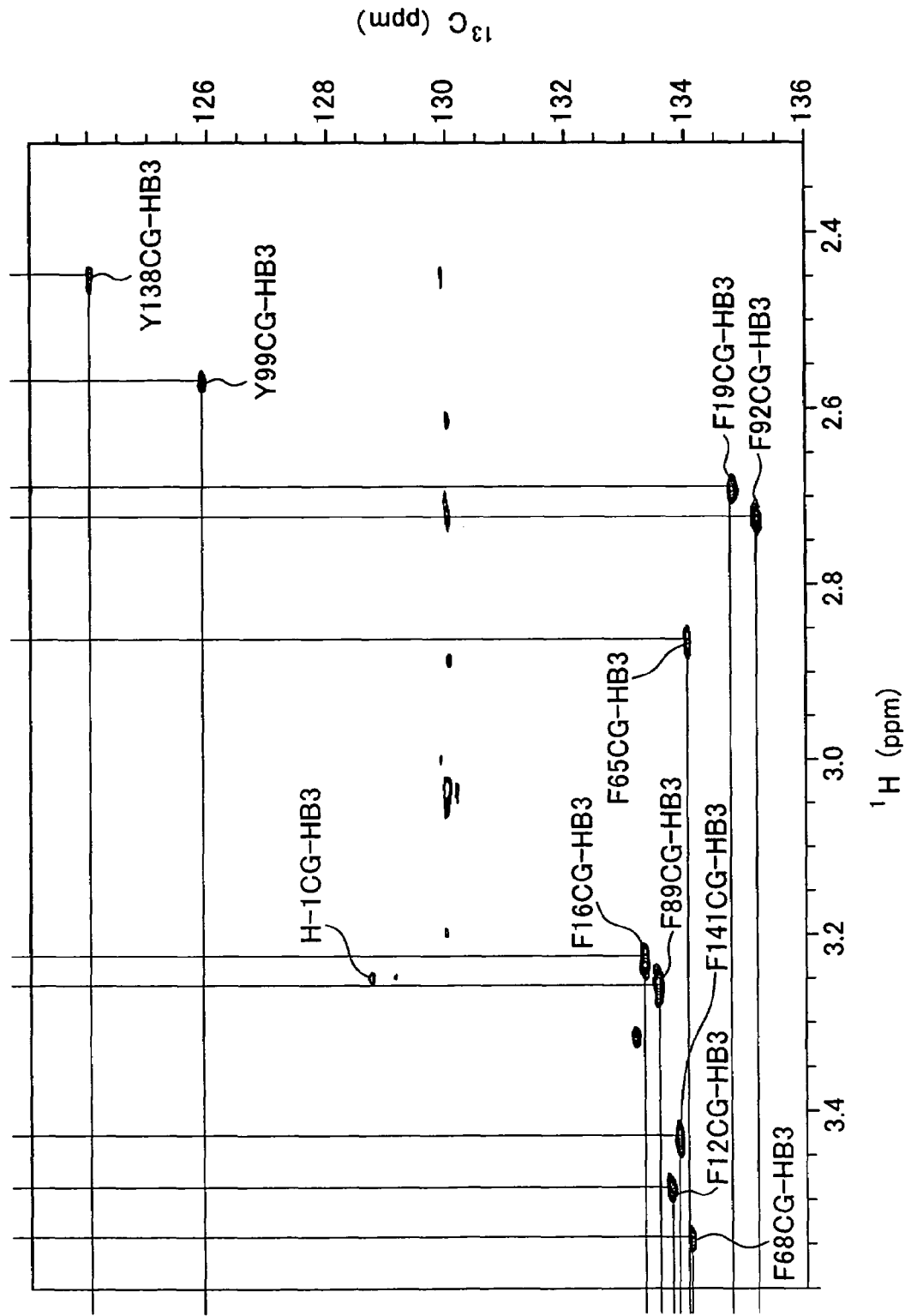

Moreover, the protons on the ring are all deuterated except for the $^{13}$C-labeled sites and therefore, any spin-spin coupling is not present between $^1$H—$^1$H. Further, the dipole-dipole interaction between $^1$H—$^1$H disappears. Accordingly, the signal width becomes quite small and the signal is quite sharp, and the measurement sensitivity is considerably improved. These sporadically labeled aromatic amino acids can considerably efficiently be applied to the $^1$H—$^{13}$C transverse relaxation optimized spectroscopy (TROSY) which is quite effective for the structural analysis of extremely high molecular weight proteins, as compared with the conventional uniformly isotope-labeled amino acid derivatives (FIG. 6). All of the NMR signals of the protons on an aromatic ring can be correlated with C β and H β through the $^{13}$C-NMR signals at γ-positions and therefore, they can in turn be correlated with the assignment of the NMR signals of main chain according to the usual method (FIGS. 7 and 8). The aromatic amino acids of type (3) have such advantages that each of them has a $^{13}$C—$^{13}$C linkage between C γ-C δ, but the carbon atom in general has a sufficiently large chemical shift and never adversely affects the magnetization-movement and that they rather permit the sequence-assignment of H δ through a large 1J ($^{13}$C—$^{13}$C). The NOE for hydrogen nucleus spatially close to the signals of the aromatic ring whose assignment has been completed can be observed using the sporadically labeled aromatic amino acids according to the 3D$^{13}$C NOESY technique including $^{13}$C-NMR chemical shift axis, while ensuring a high precision. In the usual experiments using double uniform $^{13}$C, $^{15}$N-labeled sample, all of the $^1$H-nuclei are, in principle, observed and accordingly, a larger number of NOE signals should be observed, but it would be quite difficult to observe and assign the NOE signals relating to the aromatic moieties because of a variety of problems as has been discussed above. Consequently, the NOE information obtained according to the present invention would serve as the distance-limitation quite effective for the accurate determination of the three-dimensional structures of proteins.

REFERENCE ARTICLES (1) Organic Syntheses, Coll. Vol. II, Wiley, N.Y., 126 (1943)
(2) Organic Syntheses with Isotopes, Part II, INTER-SCIENCE PUBLISHERS, INC., New York, 1388 (1958)
(3) Organic Syntheses, Coll. Vol. 78, Wiley, N.Y., 113 (2002)
(4) Wolfgang Steglich, Synthesis, 1047 (1998)
(5) E. Erlenmeyer, Ann., 275, 1 (1893)
(6) I. Ojima and M. Fujita, J. Org. Chem., 54, 4511 (1989)
(7) M. J. Burrk, J. Am. Chem. Soc., 115, 10125 (1993)
(8) Guigen Li, Dinesh Patel and Victor J. Hurby, Tetrahedron Letters, 34, 5393 (1993)
(9) K. Nishiyama and M. Kainosho, J. Labelled Compds., 9, 831(1994)
(10) V. Viswanatha and Victor J. Hurby, J. Org. Chem., 45, 2012 (1980)

What is claimed is:

1. A method for the NMR spectroscopic structural analysis of a target protein comprising the steps of incorporating into the target protein stable isotope-labeled amino acids selected from the group consisting of:

A stable isotope-labeled phenylalanine represented by the following formulae (1) to (3); and A stable isotope-labeled tyrosine represented by the following formulae (5) to (8);

and then carrying out NMR spectroscopy on the target protein to perform the structural analysis on the target protein Phenylalanine

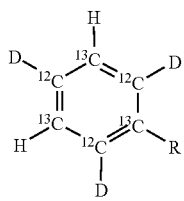
(1)

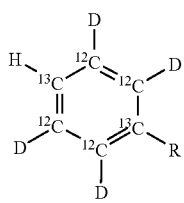
(2)

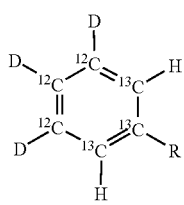
(3)

Tyrosine

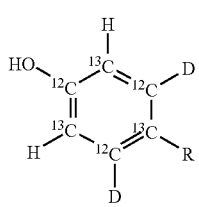
(4)

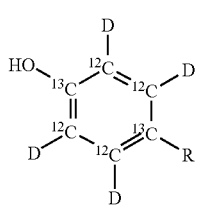
(5)

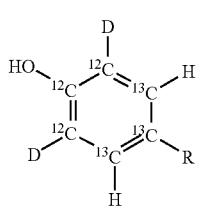
(7)

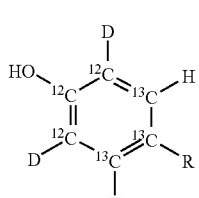
(8)

2. A method for the NMR spectroscopic structural analysis of a target protein comprising structurally analyzing, by NMR spectroscopy, a target protein whose constituent amino acids are completely replaced with stable isotope-labeled amino acids, wherein the aromatic amino acids in the target protein are selected from the group consisting of:

A stable isotope-labeled phenylalanine represented by the following formulae (1) to (3); and A stable isotope-labeled tyrosine represented by the following formulae (5) to (8);

and the aliphatic amino acids constituting the target protein are stable isotope-labeled aliphatic amino acids which satisfy the following requirements of labeled patterns:

(a) In case where a methylene group carrying two hydrogen atoms is present, one of the methylene hydrogen atoms is deuterated;

(b) In case where a prochiral gem-methyl group is present, all of the hydrogen atoms on one of the methyl groups are completely deuterated, while the hydrogen atoms on the other methyl group are partially deuterated;

(c) In case where a methyl group other than the foregoing ones is present, all of the hydrogen atoms on the methyl group except for one hydrogen atom are deuterated or all of the hydrogen atoms on the methyl group are deuterated;

(d) After the deuteration in the foregoing requirements (a), (b) and (c), all of the carbon atoms of hydrogen atom-carrying methylene and/or methyl groups are replaced with $^{13}C$ atoms; and (e) All of the nitrogen atoms present are completely replaced with $^{15}N$ atoms Phenylalanine

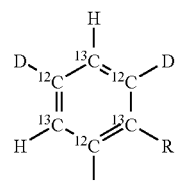 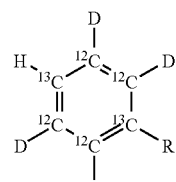
(1) (2)

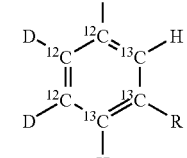 Tyrosine
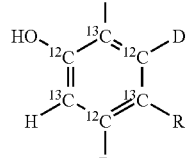
(3) (4)

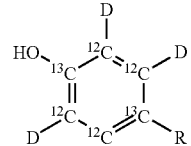 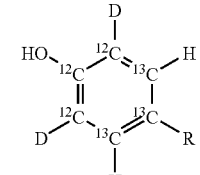
(5) (7)

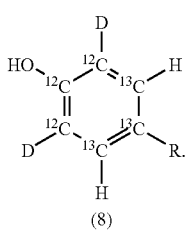
(8)

* * * * *